(12) United States Patent
Sgroi, Jr.

(10) Patent No.: US 11,357,509 B2
(45) Date of Patent: Jun. 14, 2022

(54) RELOAD ASSEMBLY FOR A CIRCULAR STAPLING DEVICE

(71) Applicant: Covidien LP, Mansfield, MA (US)

(72) Inventor: Anthony Sgroi, Jr., Wallingford, CT (US)

(73) Assignee: Covidien LP, Mansfield, MA (US)

( * ) Notice: Subject to any disclaimer, the term of this patent is extended or adjusted under 35 U.S.C. 154(b) by 66 days.

(21) Appl. No.: 16/878,025

(22) Filed: May 19, 2020

(65) Prior Publication Data

US 2021/0007745 A1 Jan. 14, 2021

Related U.S. Application Data

(60) Provisional application No. 62/872,993, filed on Jul. 11, 2019.

(51) Int. Cl.
*A61B 17/115* (2006.01)
*A61B 17/32* (2006.01)
*A61B 17/00* (2006.01)

(52) U.S. Cl.
CPC .......... *A61B 17/1155* (2013.01); *A61B 17/32* (2013.01); *A61B 2017/0046* (2013.01)

(58) Field of Classification Search
CPC ................. A61B 17/1155; A61B 17/32; A61B 2017/0046; A61B 2017/00473
USPC ........................................... 227/175.1–182.1
See application file for complete search history.

(56) References Cited

U.S. PATENT DOCUMENTS

| | | | |
|---|---|---|---|
| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |

(Continued)

FOREIGN PATENT DOCUMENTS

| CA | 908529 A | 8/1972 |
|---|---|---|
| CA | 2805365 A1 | 8/2013 |

(Continued)

*Primary Examiner* — Robert F Long

(57) ABSTRACT

A reload assembly includes a shell housing, a staple cartridge, a staple actuator, and a knife carrier. In embodiments, the knife carrier or the shell housing defines a locking groove and the other of the knife carrier and the shell housing supports a locking member. In other embodiments, the knife carrier or the staple actuator defines a locking groove and the other of the knife carrier and the staple actuator supports a locking member. The locking member is received within and movable through the locking groove to prevent readvancement of the knife carrier after the reload assembly is fired.

21 Claims, 23 Drawing Sheets

(56) References Cited

U.S. PATENT DOCUMENTS

| | | | |
|---|---|---|---|
| 4,505,414 A | 3/1985 | Filipi | |
| 4,520,817 A | 6/1985 | Green | |
| 4,550,870 A | 11/1985 | Krumme et al. | |
| 4,573,468 A * | 3/1986 | Conta | A61B 17/115 227/179.1 |
| 4,576,167 A | 3/1986 | Noiles | |
| 4,592,354 A | 6/1986 | Rothfuss | |
| 4,603,693 A | 8/1986 | Conta et al. | |
| 4,606,343 A | 8/1986 | Conta et al. | |
| 4,632,290 A | 12/1986 | Green et al. | |
| 4,646,745 A | 3/1987 | Noiles | |
| 4,665,917 A | 5/1987 | Clanton et al. | |
| 4,667,673 A | 5/1987 | Li | |
| 4,671,445 A | 6/1987 | Barker et al. | |
| 4,700,703 A | 10/1987 | Resnick et al. | |
| 4,703,887 A | 11/1987 | Clanton et al. | |
| 4,708,141 A | 11/1987 | Inoue et al. | |
| 4,717,063 A | 1/1988 | Ebihara | |
| 4,752,024 A | 6/1988 | Green et al. | |
| 4,754,909 A | 7/1988 | Barker et al. | |
| 4,776,506 A | 10/1988 | Green | |
| 4,817,847 A * | 4/1989 | Redtenbacher | A61B 17/1155 227/19 |
| 4,873,977 A | 10/1989 | Avant et al. | |
| 4,893,662 A | 1/1990 | Gervasi | |
| 4,903,697 A | 2/1990 | Resnick et al. | |
| 4,907,591 A | 3/1990 | Vasconcellos et al. | |
| 4,917,114 A | 4/1990 | Green et al. | |
| 4,957,499 A | 9/1990 | Lipatov et al. | |
| 4,962,877 A | 10/1990 | Hervas | |
| 5,005,749 A | 4/1991 | Aranyi | |
| 5,042,707 A | 8/1991 | Taheri | |
| 5,047,039 A | 9/1991 | Avant et al. | |
| 5,104,025 A | 4/1992 | Main et al. | |
| 5,119,983 A | 6/1992 | Green et al. | |
| 5,122,156 A | 6/1992 | Granger et al. | |
| 5,139,513 A | 8/1992 | Segato | |
| 5,158,222 A | 10/1992 | Green et al. | |
| 5,188,638 A | 2/1993 | Tzakis | |
| 5,193,731 A | 3/1993 | Aranyi | |
| 5,197,648 A | 3/1993 | Gingold | |
| 5,197,649 A | 3/1993 | Bessler et al. | |
| 5,205,459 A | 4/1993 | Brinkerhoff et al. | |
| 5,221,036 A | 6/1993 | Takase | |
| 5,222,963 A | 6/1993 | Brinkerhoff et al. | |
| 5,253,793 A | 10/1993 | Green et al. | |
| 5,261,920 A | 11/1993 | Main et al. | |
| 5,271,543 A | 12/1993 | Grant et al. | |
| 5,271,544 A | 12/1993 | Fox et al. | |
| 5,275,322 A | 1/1994 | Brinkerhoff et al. | |
| 5,282,810 A | 2/1994 | Allen et al. | |
| 5,285,944 A | 2/1994 | Green et al. | |
| 5,285,945 A | 2/1994 | Brinkerhoff et al. | |
| 5,292,053 A | 3/1994 | Bilotti et al. | |
| 5,309,927 A | 5/1994 | Welch | |
| 5,312,024 A | 5/1994 | Grant et al. | |
| 5,314,435 A | 5/1994 | Green et al. | |
| 5,314,436 A | 5/1994 | Wilk | |
| 5,330,486 A | 7/1994 | Wilk | |
| 5,333,773 A | 8/1994 | Main et al. | |
| 5,344,059 A | 9/1994 | Green et al. | |
| 5,346,115 A | 9/1994 | Perouse et al. | |
| 5,348,259 A | 9/1994 | Blanco et al. | |
| 5,350,104 A | 9/1994 | Main et al. | |
| 5,355,897 A | 10/1994 | Pietrafitta et al. | |
| 5,360,154 A | 11/1994 | Green | |
| 5,368,215 A | 11/1994 | Green et al. | |
| 5,392,979 A | 2/1995 | Green et al. | |
| 5,395,030 A | 3/1995 | Kuramoto et al. | |
| 5,403,333 A | 4/1995 | Kaster et al. | |
| 5,404,870 A | 4/1995 | Brinkerhoff et al. | |
| 5,411,508 A | 5/1995 | Bessler et al. | |
| 5,425,738 A | 6/1995 | Gustafson et al. | |
| 5,433,721 A | 7/1995 | Hooven et al. | |
| 5,437,684 A | 8/1995 | Calabrese et al. | |
| 5,439,156 A | 8/1995 | Grant et al. | |
| 5,443,198 A | 8/1995 | Viola et al. | |
| 5,447,514 A | 9/1995 | Gerry et al. | |
| 5,454,825 A | 10/1995 | Van Leeuwen et al. | |
| 5,464,415 A | 11/1995 | Chen | |
| 5,470,006 A | 11/1995 | Rodak | |
| 5,474,223 A | 12/1995 | Viola et al. | |
| 5,497,934 A | 3/1996 | Brady et al. | |
| 5,503,635 A | 4/1996 | Sauer et al. | |
| 5,522,534 A | 6/1996 | Viola et al. | |
| 5,533,661 A | 7/1996 | Main et al. | |
| 5,588,579 A | 12/1996 | Schnut et al. | |
| 5,609,285 A | 3/1997 | Grant et al. | |
| 5,626,591 A | 5/1997 | Kockerling et al. | |
| 5,632,433 A | 5/1997 | Grant et al. | |
| 5,639,008 A | 6/1997 | Gallagher et al. | |
| 5,641,111 A | 6/1997 | Ahrens et al. | |
| 5,658,300 A | 8/1997 | Bito et al. | |
| 5,669,918 A | 9/1997 | Balazs et al. | |
| 5,685,474 A | 11/1997 | Seeber | |
| 5,709,335 A | 1/1998 | Heck | |
| 5,715,987 A | 2/1998 | Kelley et al. | |
| 5,718,360 A | 2/1998 | Green et al. | |
| 5,720,755 A | 2/1998 | Dakov | |
| 5,732,872 A | 3/1998 | Bolduc et al. | |
| 5,749,896 A | 5/1998 | Cook | |
| 5,758,814 A | 6/1998 | Gallagher et al. | |
| 5,799,857 A | 9/1998 | Robertson et al. | |
| 5,814,055 A | 9/1998 | Knodel et al. | |
| 5,833,698 A | 11/1998 | Hinchliffe et al. | |
| 5,836,503 A | 11/1998 | Ehrenfels et al. | |
| 5,839,639 A | 11/1998 | Sauer et al. | |
| 5,855,312 A | 1/1999 | Toledano | |
| 5,860,581 A | 1/1999 | Robertson et al. | |
| 5,868,760 A | 2/1999 | McGuckin, Jr. | |
| 5,881,943 A | 3/1999 | Heck et al. | |
| 5,915,616 A | 6/1999 | Viola et al. | |
| 5,947,363 A | 9/1999 | Bolduc et al. | |
| 5,951,576 A | 9/1999 | Wakabayashi | |
| 5,957,363 A | 9/1999 | Heck | |
| 5,993,468 A | 11/1999 | Rygaard | |
| 6,024,748 A | 2/2000 | Manzo et al. | |
| 6,050,472 A | 4/2000 | Shibata | |
| 6,053,390 A | 4/2000 | Green et al. | |
| 6,068,636 A | 5/2000 | Chen | |
| 6,083,241 A | 7/2000 | Longo et al. | |
| 6,102,271 A | 8/2000 | Longo et al. | |
| 6,117,148 A | 9/2000 | Ravo et al. | |
| 6,119,913 A | 9/2000 | Adams et al. | |
| 6,126,058 A | 10/2000 | Adams et al. | |
| 6,142,933 A | 11/2000 | Longo et al. | |
| 6,149,667 A | 11/2000 | Hovland et al. | |
| 6,176,413 B1 | 1/2001 | Heck et al. | |
| 6,179,195 B1 | 1/2001 | Adams et al. | |
| 6,193,129 B1 | 2/2001 | Billner et al. | |
| 6,203,553 B1 | 3/2001 | Robertson et al. | |
| 6,209,773 B1 | 4/2001 | Bolduc et al. | |
| 6,241,140 B1 | 6/2001 | Adams et al. | |
| 6,253,984 B1 | 7/2001 | Heck et al. | |
| 6,258,107 B1 * | 7/2001 | Balazs | A61B 17/072 606/139 |
| 6,264,086 B1 | 7/2001 | McGuckin, Jr. | |
| 6,269,997 B1 | 8/2001 | Balazs et al. | |
| 6,273,897 B1 | 8/2001 | Dalessandro et al. | |
| 6,279,809 B1 | 8/2001 | Nicolo | |
| 6,302,311 B1 | 10/2001 | Adams et al. | |
| 6,338,737 B1 | 1/2002 | Toledano | |
| 6,343,731 B1 | 2/2002 | Adams et al. | |
| 6,387,105 B1 | 5/2002 | Gifford, III et al. | |
| 6,398,795 B1 | 6/2002 | McAlister et al. | |
| 6,402,008 B1 | 6/2002 | Lucas | |
| 6,439,446 B1 | 8/2002 | Perry et al. | |
| 6,443,973 B1 | 9/2002 | Whitman | |
| 6,450,390 B2 | 9/2002 | Heck et al. | |
| 6,478,210 B2 | 11/2002 | Adams et al. | |
| 6,488,197 B1 | 12/2002 | Whitman | |
| 6,491,201 B1 | 12/2002 | Whitman | |
| 6,494,877 B2 | 12/2002 | Odell et al. | |
| 6,503,259 B2 | 1/2003 | Huxel et al. | |

(56) References Cited

U.S. PATENT DOCUMENTS

| | | |
|---|---|---|
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,673,088 B1 * | 1/2004 | Vargas .................. A61B 17/11 606/185 |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |

(56) References Cited

U.S. PATENT DOCUMENTS

| | | |
|---|---|---|
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0095070 A1* | 4/2011 | Patel .................. A61B 17/105 227/181.1 |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0292368 A1* | 11/2012 | Nalagatla .......... A61B 17/1155 227/175.2 |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |

(56) References Cited

U.S. PATENT DOCUMENTS

| | | |
|---|---|---|
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2014/0197225 A1* | 7/2014 | Penna ............... A61B 17/1155 227/179.1 |
| 2014/0239046 A1* | 8/2014 | Milliman ......... A61B 17/07292 227/180.1 |
| 2015/0014393 A1* | 1/2015 | Milliman ............... A61B 90/98 227/180.1 |
| 2016/0007999 A1* | 1/2016 | Latimer ................. A61B 90/30 606/219 |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0302792 A1 | 10/2016 | Motai |
| 2018/0317920 A1* | 11/2018 | Guerrera ........... A61B 17/1155 |
| 2018/0368836 A1* | 12/2018 | Auld .................... A61B 17/072 |
| 2020/0138441 A1* | 5/2020 | Sgroi, Jr. ........... A61B 17/1155 |
| 2020/0276693 A1* | 9/2020 | Sgroi, Jr. ............... B25C 5/1617 |
| 2021/0007745 A1* | 1/2021 | Sgroi, Jr. ................ A61B 17/32 |
| 2021/0016426 A1* | 1/2021 | Sgroi, Jr. ................ B25C 5/162 |
| 2021/0022731 A1* | 1/2021 | Eisinger ............. A61B 17/0686 |
| 2021/0022732 A1* | 1/2021 | Valentine ........... A61B 17/0686 |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 2008107918 A1 | 9/2008 |

* cited by examiner

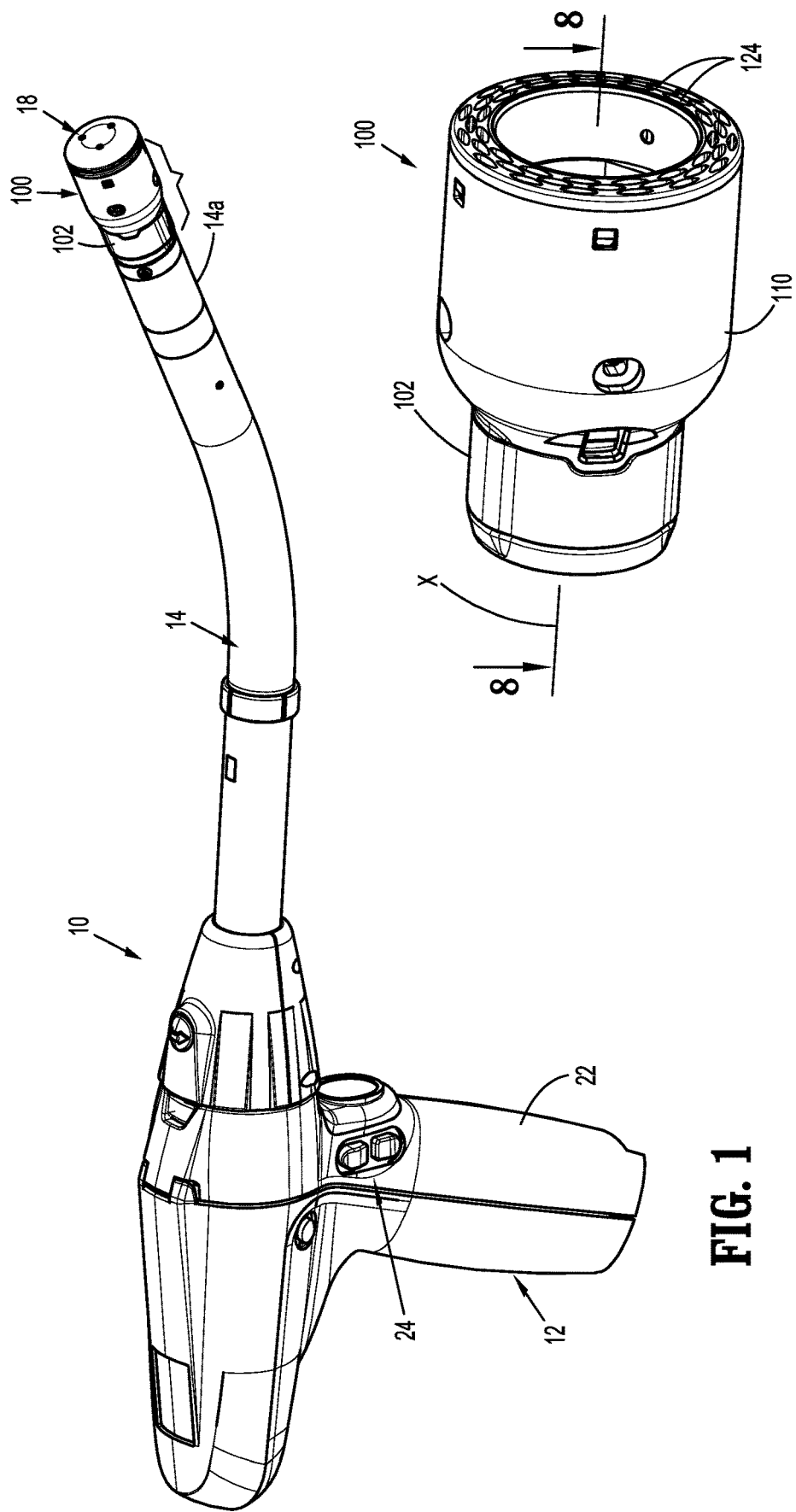

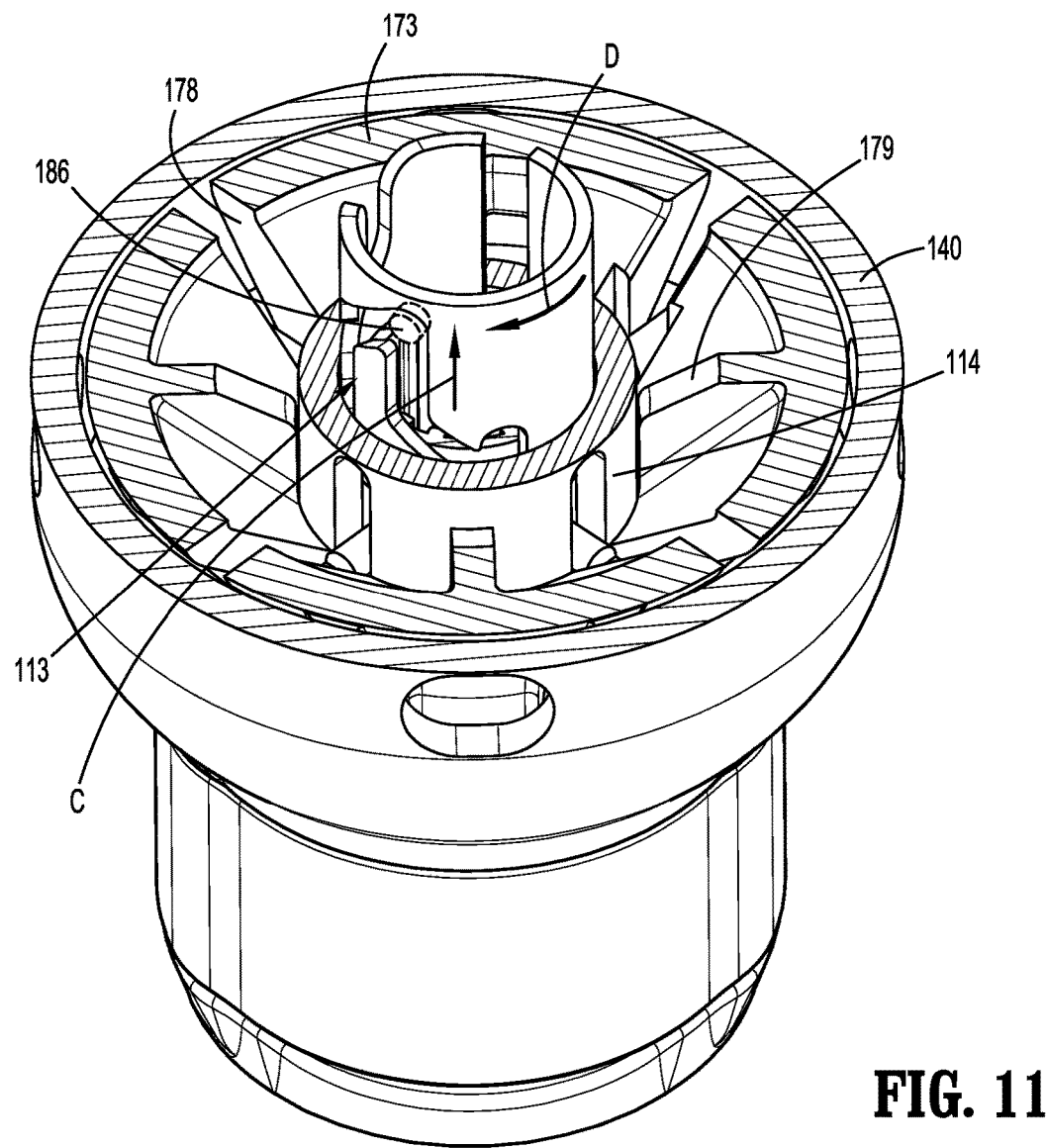
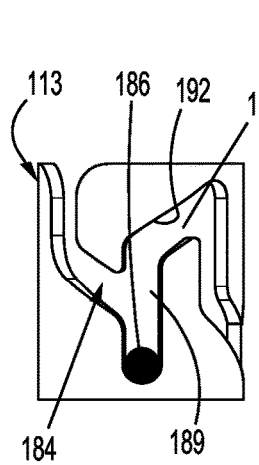 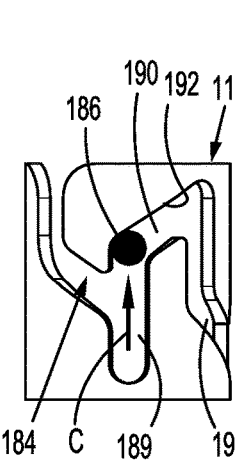 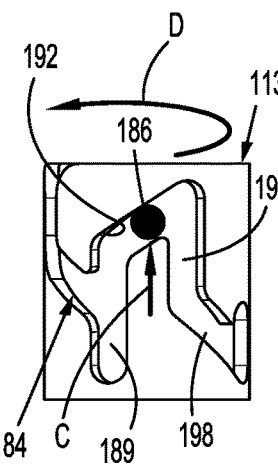 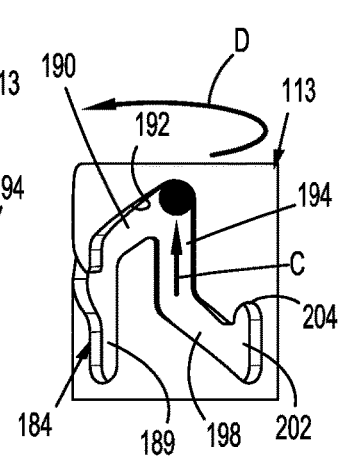
FIG. 11
FIG. 12  FIG. 13  FIG. 14  FIG. 15

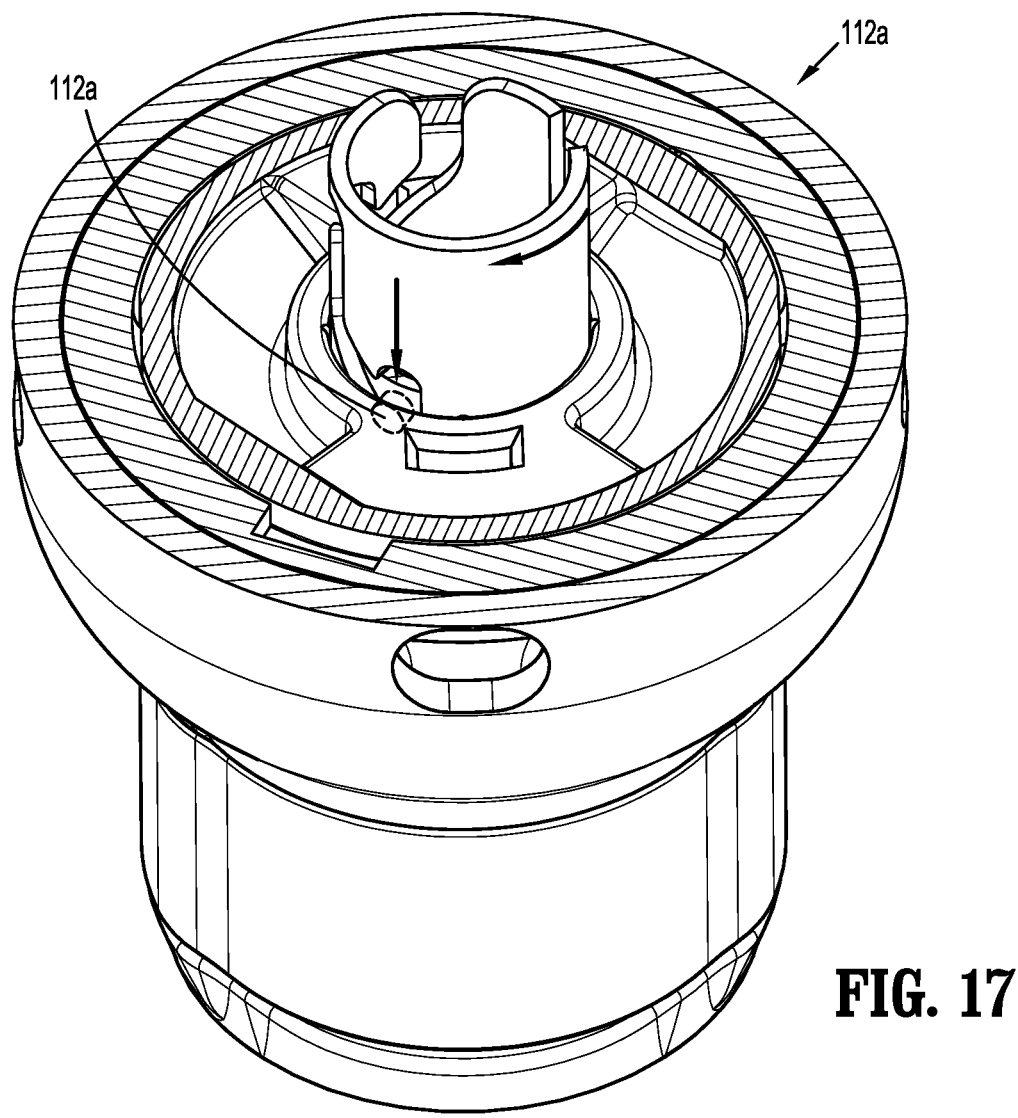
FIG. 17
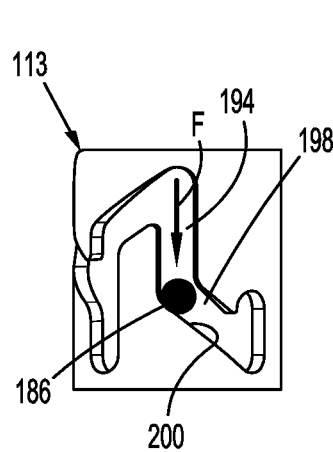
FIG. 18
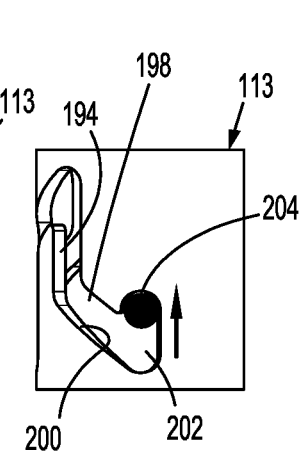
FIG. 19
FIG. 20

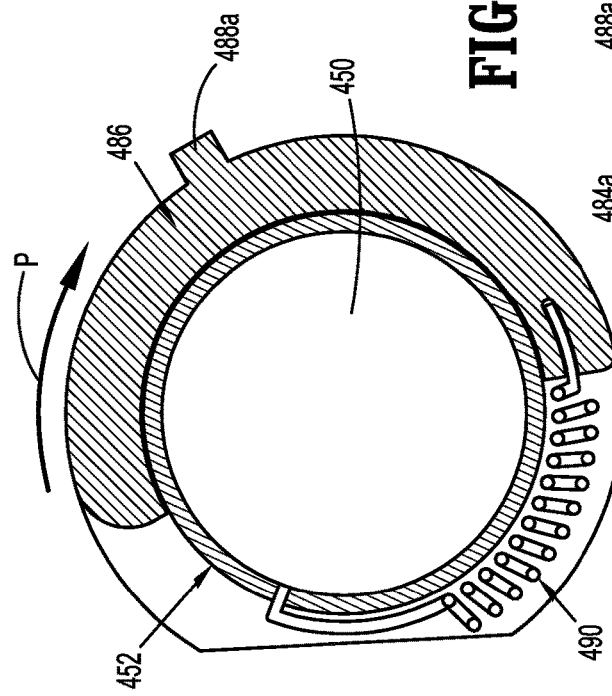
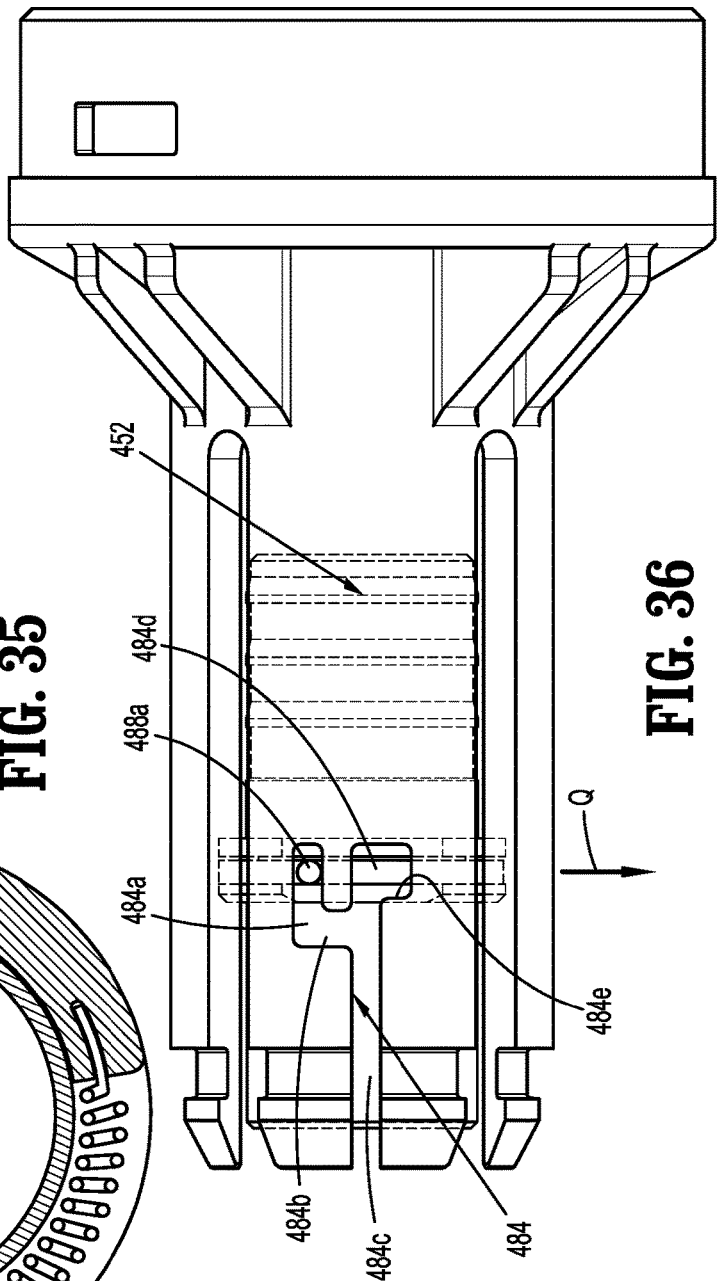
FIG. 35
FIG. 36

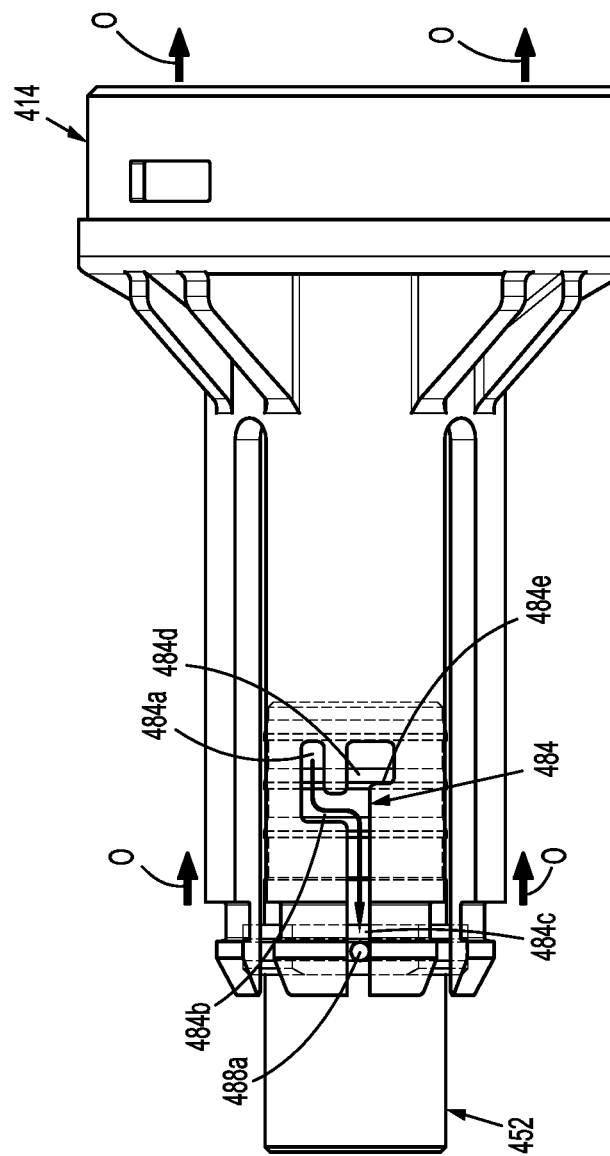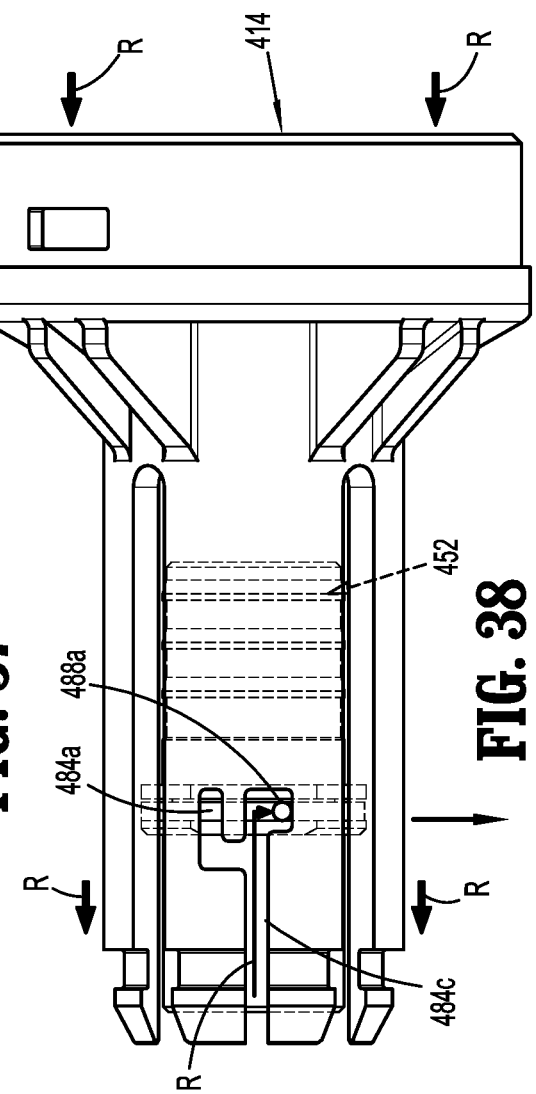

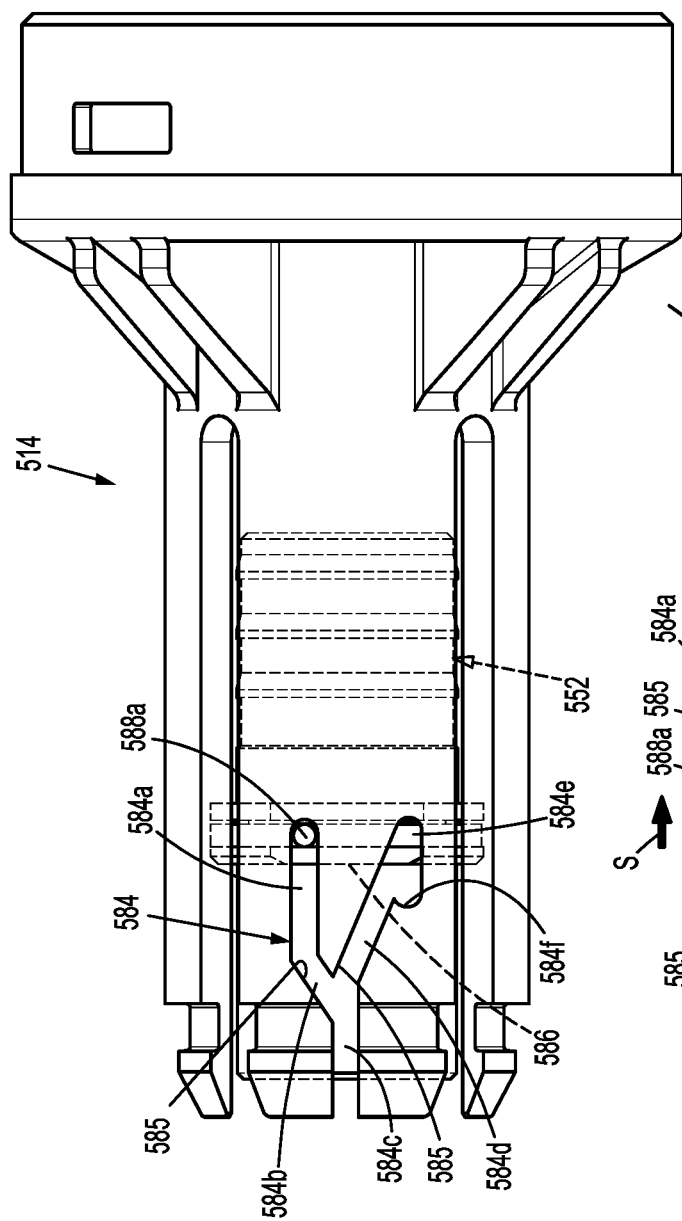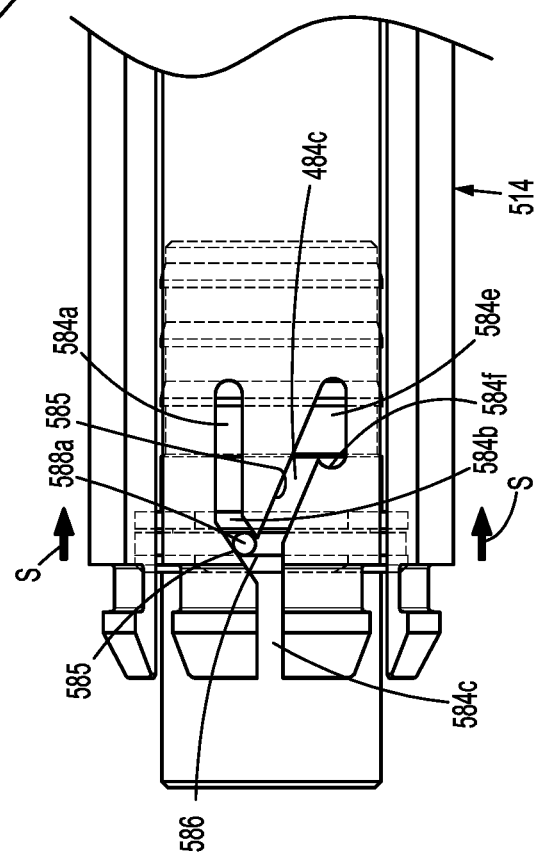

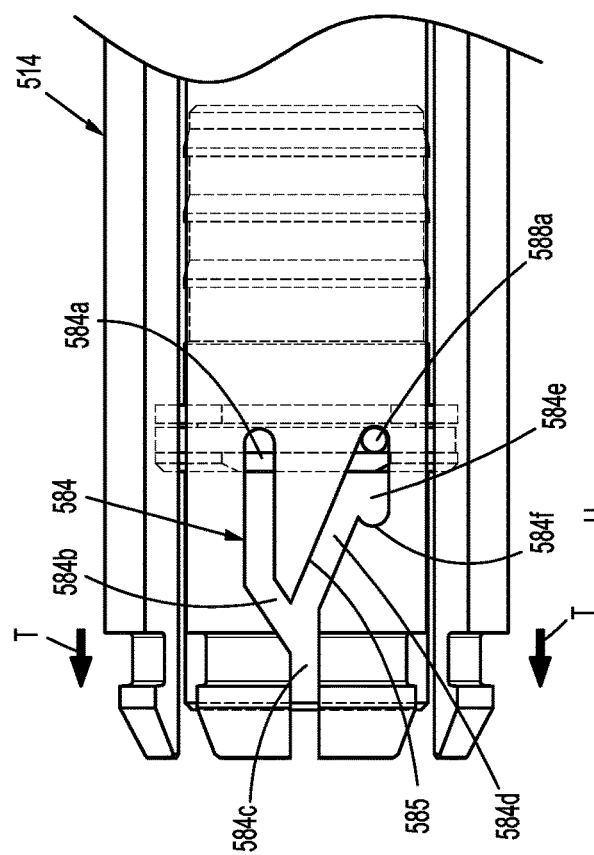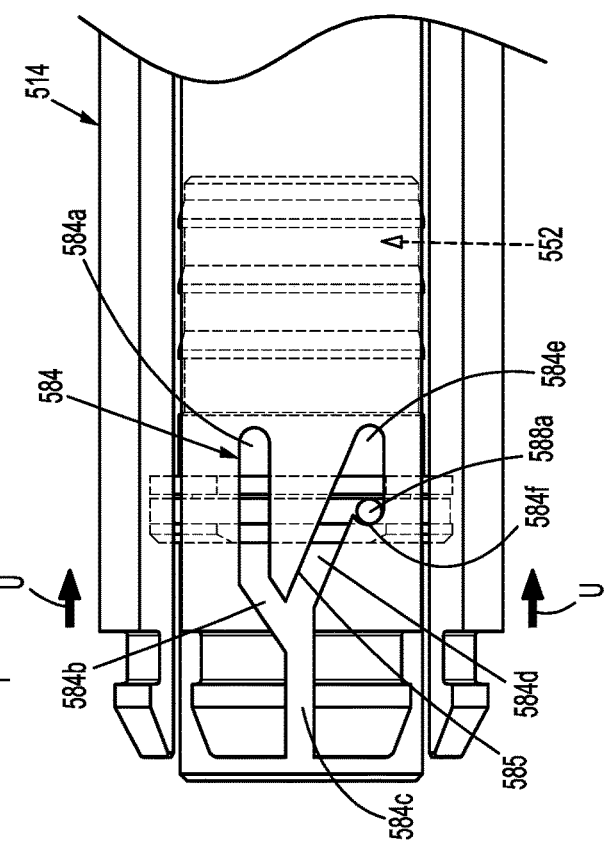

RELOAD ASSEMBLY FOR A CIRCULAR STAPLING DEVICE

CROSS-REFERENCE TO RELATED APPLICATIONS

This application claims the benefit of and priority to U.S. Provisional Patent Application Ser. No. 62/872,993 filed Jul. 11, 2019, the entire disclosure of which is incorporated by reference herein.

BACKGROUND

1. Technical Description

The present disclosure is directed to circular stapling devices and, more particularly, to reload assemblies for circular stapling devices with structure to retain a knife carrier in a retracted position after the stapling device is fired.

2. Background of Related Art

Conventional circular stapling devices include an elongate body and a shell or reload assembly that is supported on a distal portion of the elongate body. The reload assembly includes a shell housing, a staple cartridge supported on the shell housing having a plurality of staples, a pusher assembly, a knife defining a cylindrical cavity, and a knife carrier that supports the knife. The pusher assembly includes an annular pusher and a staple pushing member that is engaged with the annular pusher and is movable to move the staple pushing member to eject staples from the staple cartridge. The knife carrier is movable to advance the knife through the staple cartridge to core tissue.

After a stapling device has been operated to staple and cut tissue, the knife carrier and the knife are retracted to withdraw the knife into the shell housing. This serves two purposes. The first purpose is to move the knife to a position to allow removal of a tissue donut from within the cavity defined by the knife. The second purpose is to position the knife in a location recessed within the shell housing to avoid injury to a clinician during manipulation and disposal of the reload assembly.

A continuing need exists in the art for a reload assembly that includes improved structure for retaining the knife/knife carrier in a retracted position.

SUMMARY

One aspect of the present disclosure is directed to a reload assembly including a shell housing, a staple cartridge, a staple actuator, and a knife carrier. The shell housing includes an inner housing portion and an outer housing portion. The inner housing portion is spaced from the outer housing portion to define an annular cavity between the inner and outer housing portions. The staple cartridge is supported on a distal portion of the shell housing and defines a plurality of staple pockets. Each of the staple pockets receives a staple. The staple actuator is supported within the annular cavity and is movable between a retracted position and an advanced position to eject the staples from the staple cartridge. The knife carrier includes a body defining a longitudinal axis and supports a knife. The body of the knife carrier includes an inner wall defining a central bore. The inner housing portion of the shell housing is positioned within the central bore of the knife carrier such that the knife carrier is movable about the inner housing portion of the shell housing between advanced and retracted positions. One of the knife carrier and the shell housing defines a locking groove and the other of the knife carrier and the shell housing supports a locking member, wherein the locking member is received within and movable through the locking groove to prevent advancement of the knife carrier after the reload assembly is fired.

In embodiments, the locking groove has a first end and a second end, wherein the second end of the locking groove defines a stop surface that is positioned to engage the locking member when the locking member is returned to its retracted position after the reload assembly is fired.

In some embodiments, a locking collar is supported on the inner housing portion and the locking groove is defined in the locking collar.

In certain embodiments, the locking member includes a protrusion that is supported on the knife carrier and is received within the locking groove of the locking collar.

In embodiments, the locking collar is rotatably supported on the inner housing portion of the shell housing from an unlocked position to a locked position in response to movement of the knife carrier between its advanced and retracted positions.

In some embodiments, the locking collar is axially fixed about the inner housing portion of the shell housing.

In certain embodiments, the locking groove is defined in the inner housing portion of the shell housing and the locking member is supported on the knife carrier.

In embodiments, the locking member includes a resilient C-shaped body having spaced ends, wherein the C-shaped body is supported on the knife carrier and at least one of the spaced ends is positioned within the central bore of the knife carrier and is received within the locking groove.

In some embodiments, the locking groove includes a first locking groove defined in one side of the inner housing portion of the shell housing and a second locking groove defined in an opposite side of the inner housing portion of the shell housing, wherein each of the first and second locking grooves receives one of the spaced ends of the C-shaped body.

In certain embodiments, the locking groove includes a first linear portion, a second linear portion, and a stop surface positioned at one end of the second linear portion, wherein the first linear portion intersects the second linear portion.

In embodiments, the stop surface is defined within a locking bore.

In some embodiments, the first linear portion has a first depth, the second linear portion has a second depth, and the locking bore has a third depth, wherein the second depth is greater than the first depth and the third depth is greater than the second depth.

In certain embodiments, the locking groove is defined in the knife carrier and the locking member is supported on the inner housing portion of the shell housing.

In embodiments, the locking member is rotatably supported on the inner housing portion of the shell housing and includes a protrusion that is received within the locking groove, wherein the locking member is rotatable from an unlocked position to a locked position in which the protrusion is aligned with the stop surface.

In some embodiments, a biasing member is positioned to urge the locking member towards the locked position.

In certain embodiments, the locking groove includes a first linear portion, a first transverse portion, a second linear portion, a second transverse portion, and a lockout portion, and the stop surface is positioned within the lockout portion.

In embodiments, the inner housing portion of the shell housing includes cam surfaces that define at least a portion of the first and second transverse portions of the locking groove, wherein the cam surfaces engage the protrusion of the locking member to move the locking member towards the locked position in response to movement of the knife carrier between the retracted and advanced position.

Another aspect of the present disclosure is directed to a reload assembly including a shell housing, a staple cartridge, a staple actuator, and a knife carrier. The shell housing includes an inner housing portion and an outer housing portion. The inner housing portion is spaced from the outer housing portion to define an annular cavity between the inner and outer housing portions. The staple cartridge is supported on a distal portion of the shell housing and defines a plurality of staple pockets. Each of the staple pockets receives a staple. The staple actuator is supported within the annular cavity and is movable between a retracted position and an advanced position to eject the staples from the staple cartridge. The knife carrier includes a body defining a longitudinal axis and supports a knife. The body of the knife carrier includes an inner wall defining a central bore. The inner housing portion of the shell housing is positioned within the central bore of the knife carrier such that the knife carrier is movable about the inner housing portion of the shell housing between advanced and retracted positions. One of the knife carrier and the staple actuator defines a locking groove and the other of the knife carrier and the staple actuator supports a locking member. The locking member is received within and movable through the locking groove to prevent readvancement of the knife carrier after the reload assembly is fired.

In embodiments, the locking groove has a first end and a second end and the second end of the locking groove defines a stop surface that is positioned to engage the locking member when the locking member is returned to its retracted position after the reload assembly is fired to obstruct readvancement of the knife carrier.

In some embodiments, the locking member includes a protrusion supported within a channel defined in the knife carrier.

In certain embodiments, the channel is elongated to allow for lateral movement of the protrusion within the channel in response to movement of the knife carrier between its advanced and retracted positions.

BRIEF DESCRIPTION OF THE DRAWINGS

Various embodiments of the presently disclosed reload assembly are described herein below with reference to the drawings, wherein:

FIG. 1 is a side perspective view of a circular stapling device including an exemplary embodiment of the presently disclosed reload assembly in accordance with the present disclosure;

FIG. 2 is a side perspective view of the reload assembly of FIG. 1;

FIG. 11 is a cross-sectional view taken along section line 11-11 of FIG. 10;

FIG. 12 is a schematic view of the locking collar and a pin of the knife carrier shown in FIG. 3 with the knife carrier in the pre-fired position;

FIG. 13 is a schematic view of the locking collar and the pin of the knife carrier shown in FIG. 3 as the knife carrier moves towards the fired position;

FIG. 14 is a schematic view of the locking collar and the pin of the knife carrier as the knife carrier moves further towards the fired position;

FIG. 15 is a schematic view of the locking collar and the pin of the knife carrier with the knife carrier in its advanced, fired position;

FIG. 17 is a cross-sectional view taken along section line 17-17 of FIG. 16;

FIG. 18 is a schematic view of the locking collar and the pin of the knife carrier after the reload assembly is fired as the knife carrier moves towards its retracted position;

FIG. 19 is a schematic view of the locking collar and the pin of the knife carrier after the reload assembly is fired with the knife carrier in its retracted position;

FIG. 20 is a schematic view of the locking collar and the pin of the knife carrier after the reload assembly is fired with the knife carrier in a locked position;

FIG. 35 is a cross-sectional view taken along section line 35-35 of FIG. 33;

FIG. 36 is a side perspective view of the knife carrier of the reload assembly shown in FIG. 32 with the bushing and snap ring assembly shown in phantom and the knife carrier in a pre-fired retracted position;

FIG. 37 is a side perspective view of the knife carrier of the reload assembly shown in FIG. 36 with the bushing and snap ring assembly shown partially in phantom and the knife carrier an advanced position;

FIG. 38 is a side perspective view of the knife carrier of the reload assembly shown in FIG. 37 with the bushing and snap ring assembly shown in phantom and the knife carrier a fired retracted position;

FIG. 39 is an alternative embodiment of the knife carrier and the bushing and snap ring assembly shown in FIG. 36 with the knife carrier in a pre-fired retracted position and the bushing and snap ring assembly shown in phantom;

FIG. 40 is a side perspective view of the knife carrier of the reload assembly and the bushing and snap ring assembly shown in FIG. 39 with the bushing and snap ring assembly shown partially in phantom and the knife carrier moving towards its advanced position;

FIG. 40 is a side perspective view of the knife carrier of the reload assembly and the bushing and snap ring assembly shown in FIG. 39 with the bushing and snap ring assembly shown partially in phantom and the knife carrier in its advanced position;

FIG. 43 is a side perspective view of the knife carrier of the reload assembly and the bushing and snap ring assembly shown in FIG. 42 with the bushing and snap ring assembly shown partially in phantom and the knife carrier in its retracted position after firing of the reload assembly; and FIG. 44 is a side perspective view of the knife carrier of the reload assembly and the bushing and snap ring assembly shown in FIG. 43 with the bushing and snap ring assembly shown partially in phantom and the knife carrier locked out.

DETAILED DESCRIPTION OF EMBODIMENTS

Figure 3:
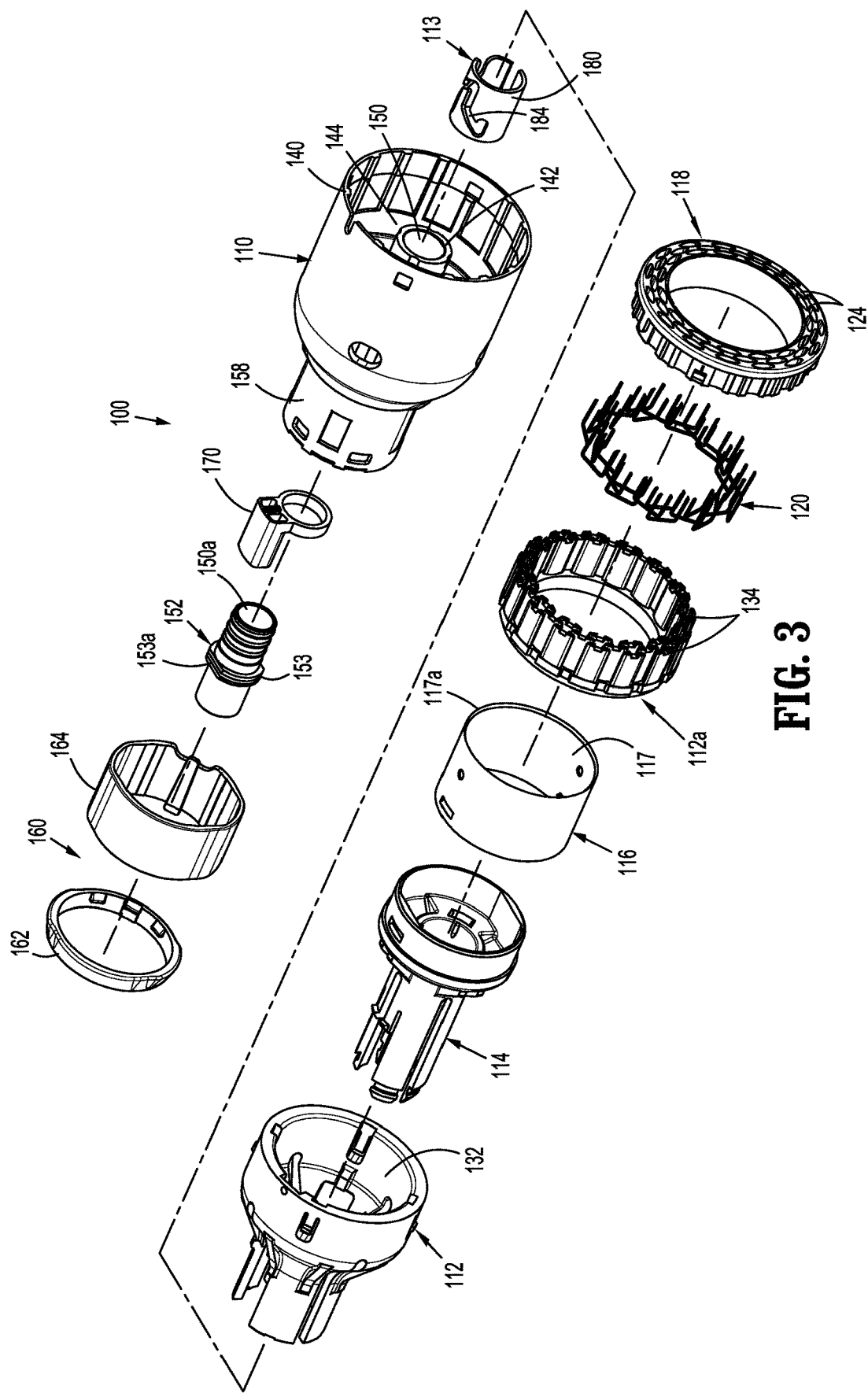
FIG. 3 is an exploded side perspective view of the reload assembly of FIG. 2.

The presently disclosed reload assembly will now be described in detail with reference to the drawings in which like reference numerals designate identical or corresponding elements in each of the several views. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the term "endoscopic" is used generally used to refer to endoscopic, laparoscopic, arthroscopic, and/or any other procedure conducted through small diameter incision or cannula. Further, the term "clinician" is used generally to refer to medical personnel including doctors, nurses, and support personnel.

FIGS. 1 and 2 illustrate a circular stapling device 10 including an exemplary embodiment of the presently disclosed reload assembly shown generally as reload assembly 100. The reload assembly 100 defines a longitudinal axis "X" (FIG. 2). The stapling device 10 includes a handle assembly 12, an elongate body or adaptor assembly 14, the reload assembly 100, and an anvil assembly 18. The anvil assembly 18 is supported for movement in relation to the reload assembly 100 between spaced and approximated positions as is known in the art. The reload assembly 100 includes a proximal portion 102 that is releasably coupled to a distal portion 14a of the elongate body 14. The handle assembly 12 includes a stationary grip 22 that supports actuation buttons 24 for controlling operation of various functions of the stapling device 10 including approximation of the reload and anvil assemblies 100 and 18, respectively, firing of staples from the reload assembly 100, and cutting or coring of tissue.

The stapling device 10 is illustrated as an electrically powered stapling device including an electrically powered handle assembly 12 that may support one or more batteries (not shown). The elongate body 14 is in the form of an adaptor assembly that translates power from the handle assembly 12 to the reload and anvil assemblies 100, 18, respectively. Examples of electrically powered stapling devices can be found in U.S. Pat. No. 9,055,943 (the '943 Patent), U.S. Pat. No. 9,023,014 (the '014 Patent), and U.S. Publication Nos. 2018/0125495, and 2017/0340351 which are incorporated herein by reference in their entirety. Alternately, it is envisioned that the present disclosure could also be incorporated into a manually powered stapling device such as disclosed in U.S. Pat. No. 7,303,106 (the '106 Patent) or a stapling device that is configured for use with a robotic system such as disclosed in U.S. Pat. No. 9,962,159 (the '159 Patent) that does not include a handle assembly. The '106 and '159 Patents are also incorporated herein by reference in their entirety.

Figure 8:
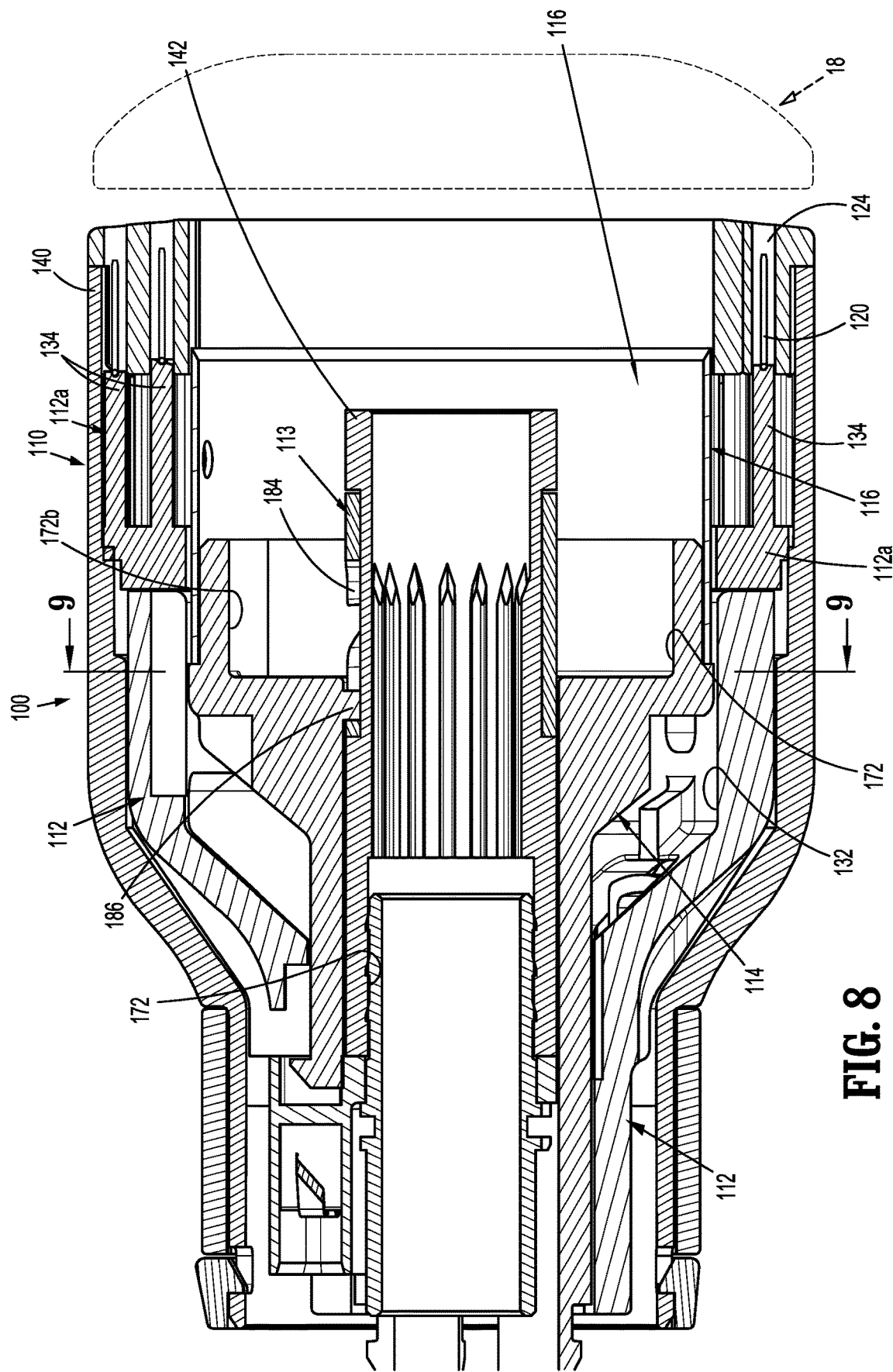
FIG. 8 is a cross-sectional view taken along section line 8-8 of FIG. 2 with the reload assembly in a pre-fired position.

Referring to FIGS. 2 and 3, the reload assembly 100 includes a shell housing 110, a staple actuator 112, a locking collar 113, a staple pushing member 112a, a knife carrier 114, an annular knife 116 supported on the knife carrier 114, a staple cartridge 118, and a plurality of staples 120 supported within the staple cartridge 118. The staple cartridge 118 is annular and defines annular rows of staple pockets 124. Each of the staple pockets 124 supports one of the plurality of staples 120. The staple actuator 112 and the staple pushing member 112a together define a longitudinal through bore 132 (FIG. 8). The staple actuator 112 has a distal portion that abuts a proximal portion of the staple pushing member 112a such that distal movement of the staple actuator 112 within the shell housing 110 causes distal movement of the staple pushing member 112a within the shell housing 110. The staple pushing member 112a of the reload 100 has a plurality of fingers 134. Each of the plurality of fingers 134 is received within a respective one of the staple pockets 124 of the staple cartridge 118 and is movable through the respective staple pocket 124 to eject the staples 120 from the staple pockets 124 when the staple pushing member 130 is moved from a retracted position to an advanced position within the shell housing 110.

The shell housing 110 includes an outer housing portion 140 and an inner housing portion 142 that are spaced from each other to define an annular cavity 144 between the inner and outer housing portions 140 and 142. The staple actuator 112, the staple pushing member 112a, the knife carrier 114, and the annular knife 116 are movable within the annular cavity 144 of the shell housing 110 between retracted and advanced positions. The staple actuator 112 and the staple pushing member 112a are movable from their retracted positions to their advanced positions independently of the knife carrier 114 and annular knife 116 to eject the staples 120 from the staple cartridge 118. The annular knife 116 is supported about an outer surface of the knife carrier 114 and defines a cylindrical cavity 117 and a distal cutting edge 117a. After the staple actuator 112 and staple pushing member 112a are moved from their retracted positions to their advanced positions, the knife carrier 114 can be moved from its retracted position to its advanced position to cut tissue positioned radially inward of the staple cartridge 118.

Figure 5:
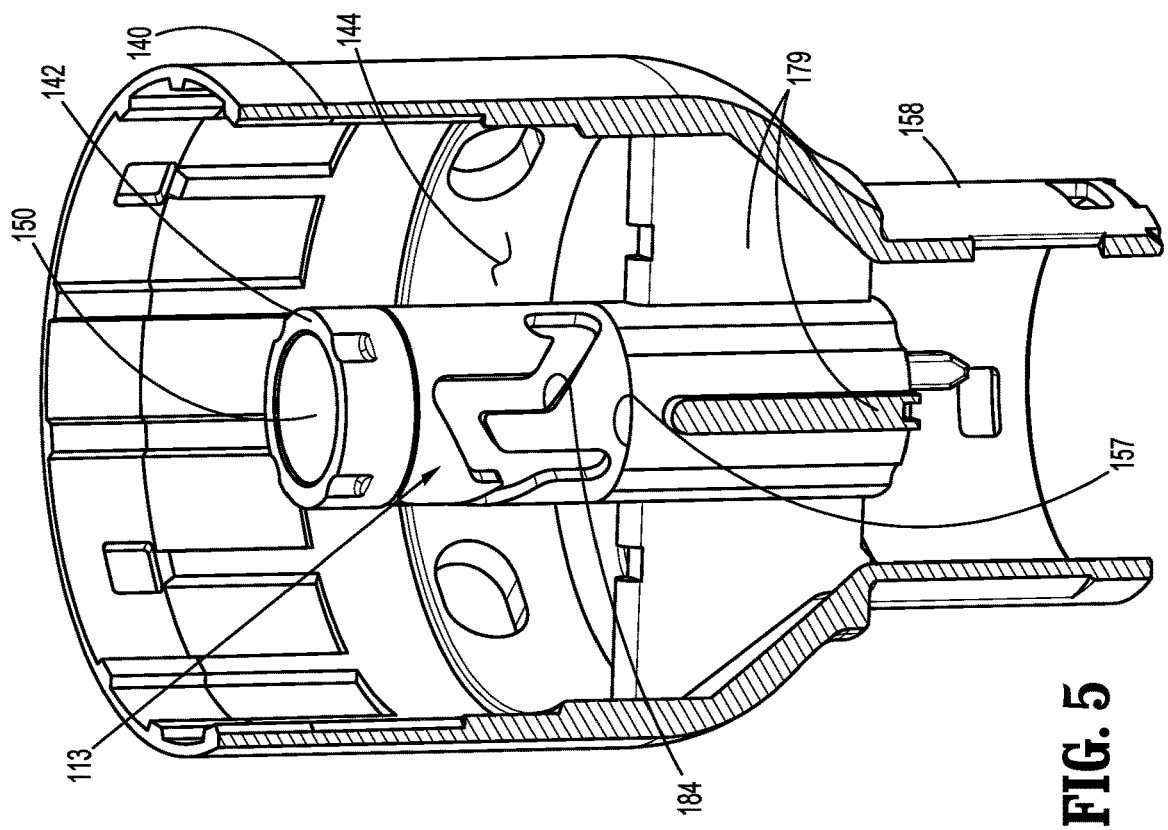
FIG. 5 is a perspective cross-sectional view of the shell housing and the locking collar shown in FIG. 4 with the parts assembled.
Figure 4:
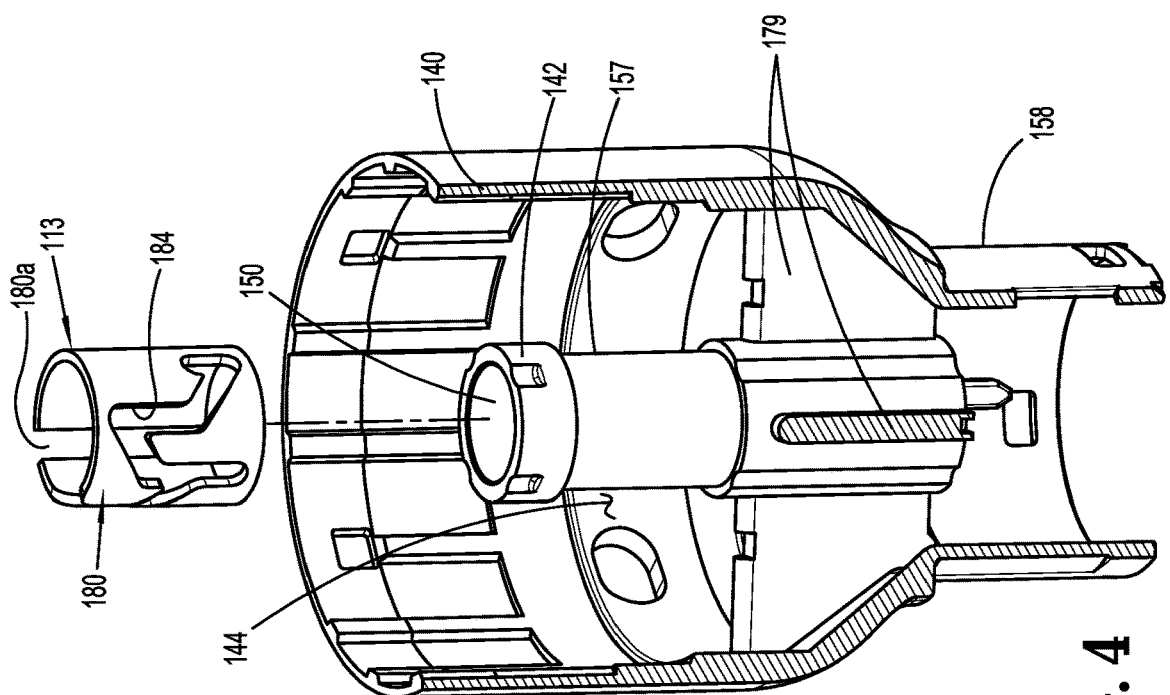
FIG. 4 is a perspective cross-sectional view of a shell housing and locking collar of the reload assembly shown in FIG. 3 with parts separated.

Referring to FIGS. 3-5, the inner housing portion 142 of the shell housing 110 defines a through bore 150 (FIG. 3) that receives an anvil shaft (not shown) of the anvil assembly 18. For a more detailed description of an exemplary anvil assembly 18, see, e.g., the '106 Patent. The through bore 150 has a proximal portion that receives a bushing 152 (FIG. 3) that defines a through bore 150a that is coaxial and forms an extension of the through bore 150 of the inner housing portion 142 of the shell housing 110. In embodiments, the bushing 152 is formed of a high strength material, e.g., metal, to provide added strength to the inner housing portion 142 of the shell housing 110 and includes an annular flange 153 (FIG. 3) that defines an annular recess 153a. The inner housing portion 142 of the shell housing 110 includes an outer surface that defines an annular recess 157 (FIG. 4) that receives the locking collar 113 as described in further detail below.

The shell housing 110 includes a proximal portion 158 that supports a coupling mechanism 160 (FIG. 3). The coupling mechanism 160 is operable to releasably couple the reload assembly 100 to the adaptor assembly 14 of the stapling device 10 (FIG. 1) to facilitate replacement of the reload assembly 100 and reuse of the stapling device 10. The coupling mechanism 160 includes a retaining member 162 and a coupling member 164. The coupling member 164 is received about the proximal portion 158 of the shell housing 110 and is configured to engage the distal portion 114a (FIG. 1) of the adaptor assembly 14 to couple the adaptor assembly 14 to the reload assembly 100. It is envisioned that other coupling mechanisms can be used to secure the reload assembly 100 to the adaptor 14.

The reload assembly 100 may include an e-prom holder 170 (FIG. 3) that is supported on the shell housing 110 to support an e-prom (not shown). As is known in the art, an e-prom communicates with the adaptor assembly 14 to provide information to the adaptor assembly 14 and the handle assembly 12 related to characteristics of the reload assembly 10.

The locking collar 113 includes an annular body 180 that defines a longitudinal axis and a through bore 182. The longitudinal axis of the locking collar 113 is coaxial with the longitudinal axis "X" (FIG. 2) of the reload assembly 100. The annular body 180 is received within the annular recess 157 about the inner housing portion 142 of the shell assembly 110. In embodiments, the body 180 defines a longitudinal split 180a and is formed from a resilient material. The longitudinal split 180a allows the body 180 to be deformed and placed about the inner housing portion 142 of the shell assembly 110 within the annular recess 157 such that the body 180 can rotate about the longitudinal axis "X" (FIG. 2) within the annular recess 157. The body 180 has a length that is substantially equal to the length of the annular recess 157 to minimize longitudinal movement of the locking collar 113 within the annular recess 157 of the inner housing portion 142 of the shell housing 110.

Figure 10:
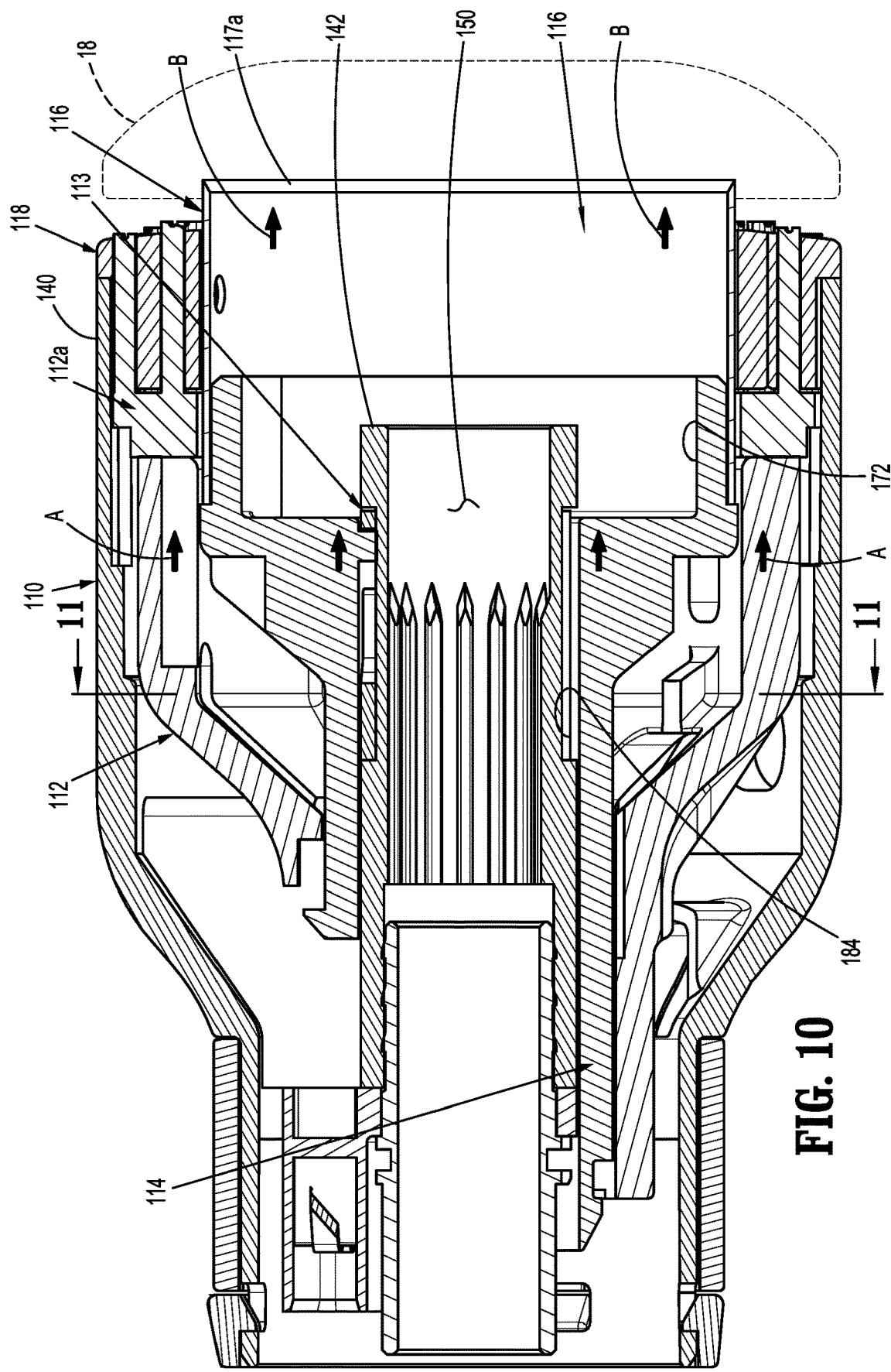
FIG. 10 is a cross-sectional view taken along section line 8-8 of FIG. 2 with the reload assembly in a fired position and the knife carrier in an advanced position.

The locking collar 113 defines a locking groove 184 that is configured to lock the knife carrier 114 in a post-fired retracted position after the knife carrier 114 moves from a pre-fired retracted position (FIGS. 8 and 12), to an advanced position (FIGS. 10 and 15), and back to the post-fired retracted position (FIGS. 16 and 19) as described in further detail below.

Figure 7:
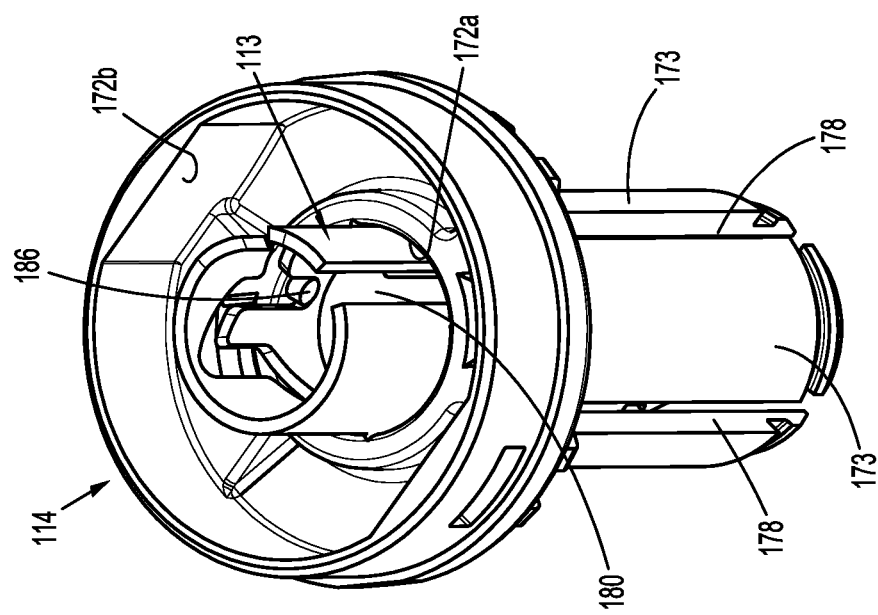
FIG. 7 is a perspective view from the distal end of the knife carrier shown in FIG. 6 with the locking collar received within a central bore of the knife carrier and the knife carrier in a pre-fired position.
Figure 6:
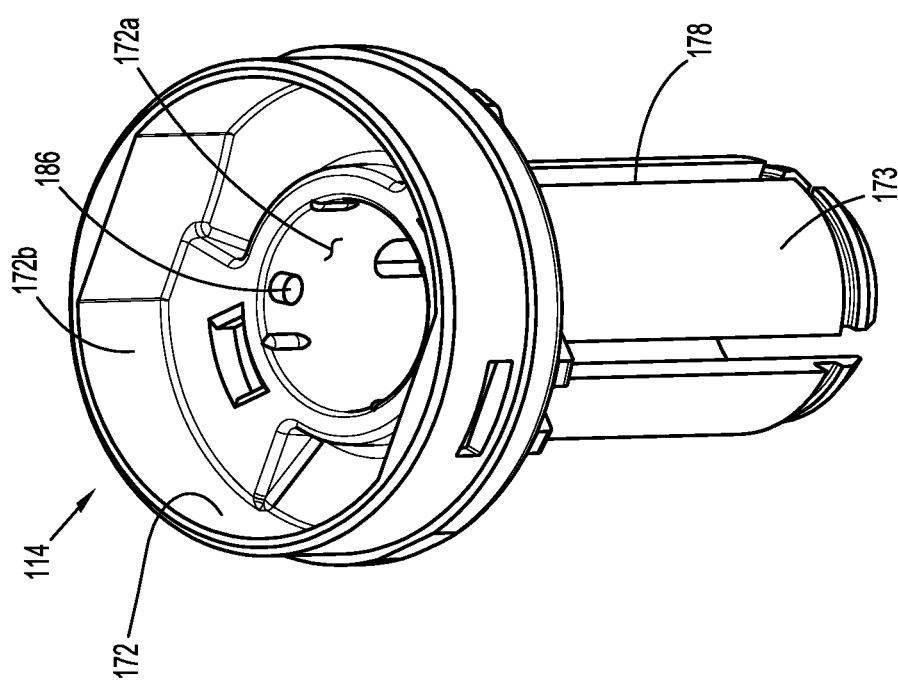
FIG. 6 is a perspective view from the distal end of a knife carrier of the reload assembly shown in FIG. 3.

Referring to FIGS. 6 and 7, the knife carrier 114 defines a stepped central bore 172 and is movably positioned within the through bore 132 (FIG. 8) defined by the staple actuator 112 and the pushing member 112a between its retracted and advanced positions. The stepped central bore 172 includes a small diameter proximal portion 172a and a larger diameter distal portion 172b that receives the knife 116. The proximal portion 172a of the central bore 172 of the knife carrier 114 is defined by longitudinally extending body portions 173 that are separated by longitudinal slots 178 and receive the inner housing portion 142 (FIG. 8) of the shell housing 110 such that the knife carrier 114 slides about the inner housing portion 142. The longitudinal slots 178 receive guide portions 179 (FIG. 4) of the shell housing 110 to limit the knife carrier 114 to longitudinal movement within the annular cavity 144 of the shell housing 110 as the knife carrier 114 moves between its advanced and retracted positions. At least one of the body portions 173 includes an inner surface 173a that supports a locking member 186 at a fixed location within the central bore 172. In embodiments, the locking member 186 includes a protrusion that extends into the central bore 172 of the knife carrier 114.

Figure 9:
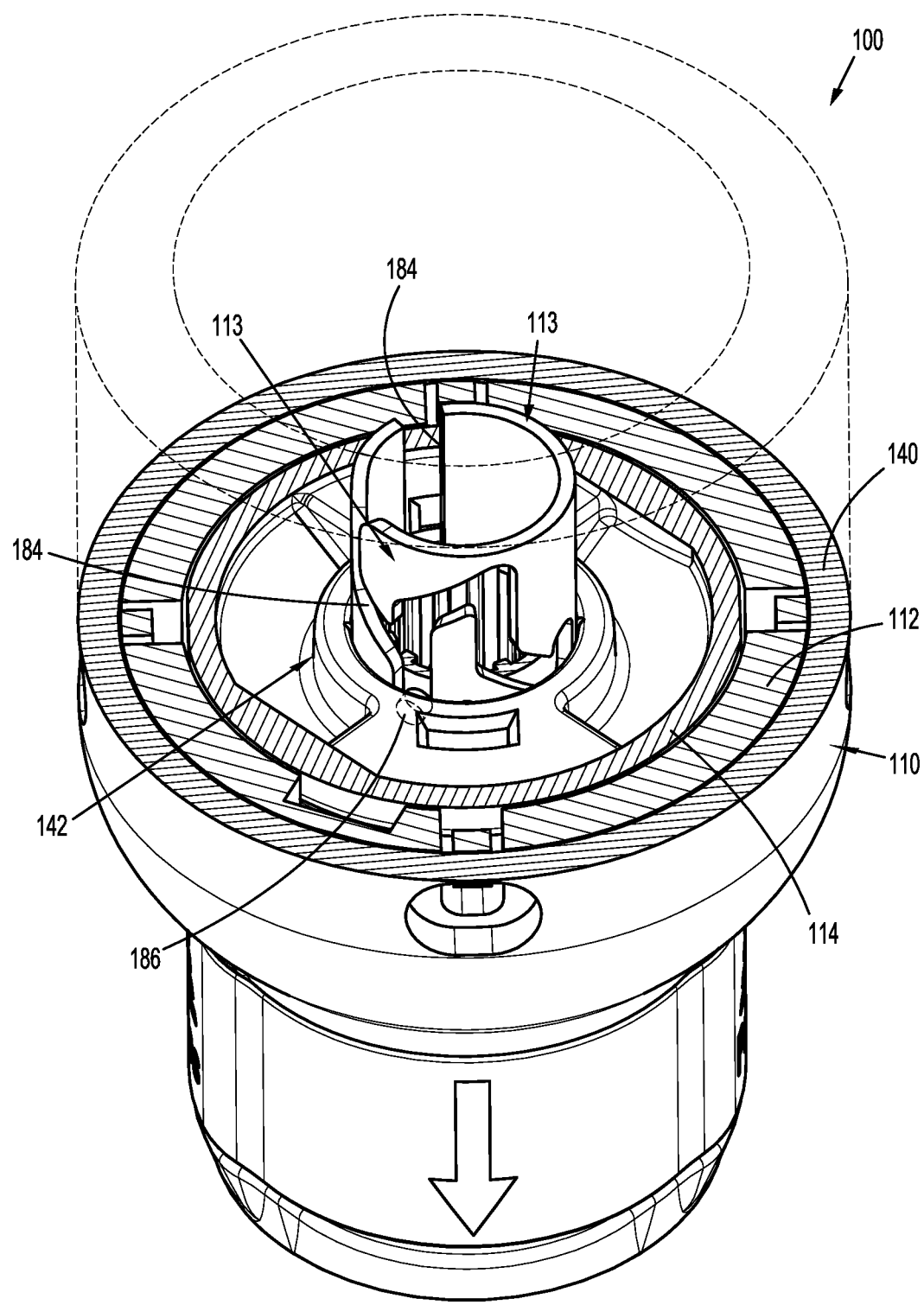
FIG. 9 is a cross-sectional view taken along section line 9-9 of FIG. 8.

Referring to FIGS. 7-9, when the knife carrier 114 is in a retracted position (FIG. 8), the locking member 186 of the knife carrier 114 is received within a proximal end of the locking groove 184 of the locking collar 113. As described above, the locking collar 113 is longitudinally fixed about the inner housing portion 142 of the shell housing 110 but is free to rotate about the inner housing portion 142.

Referring to FIGS. 10-15, when the surgical stapling device 10 is actuated via the handle assembly 12 (FIG. 1), the staple actuator 112 is moved from its retracted position to its advanced position to advance the staple pushing member 112a to eject staples 120 (FIG. 8) from the staple cartridge 118 into the anvil assembly 18. After the staples 120 are ejected from the staple cartridge 118, the stapling device 10 is actuated via the handle assembly 12 (FIG. 1) to advance the knife carrier 114 in the direction indicate by arrows "A" in FIG. 10 about the inner housing portion 142 of the shell housing 110. Advancement of the knife carrier 114 advances the knife 116 in the direction indicated by arrows "B" in FIG. 10. As the knife carrier 114 is moved in relation to the inner housing portion 142, the locking member 186 translates within the locking groove 184 of the locking collar 113 in the direction indicated by arrows "C" in FIGS. 13-15 through a first axial portion 189 of the locking groove 184 from the proximal end (FIG. 12) of the locking groove 184 to a distal end (FIG. 15) of the locking groove 184.

Referring to FIGS. 13 and 14, the locking groove 184 has a first transverse portion 190 that communicates with the first axial portion 189 and is defined by a first cam surface 192. The first cam surface 192 defines an acute angle with the longitudinal axis "X" (FIG. 2) of the reload assembly 100. As the locking member 184 translates through the locking groove 184 in the direction indicated by arrows "C" in FIG. 13, the locking member 186 engages the first cam surface 192 to rotate the locking collar 113 in the direction indicated by arrows "D" in FIGS. 14 and 15 about the inner housing portion 142 of the shell housing 110. When the knife carrier 114 is in its advanced position (FIG. 15), the locking member 186 is aligned within a second axial portion 194 of the locking groove 184.

Figure 16:
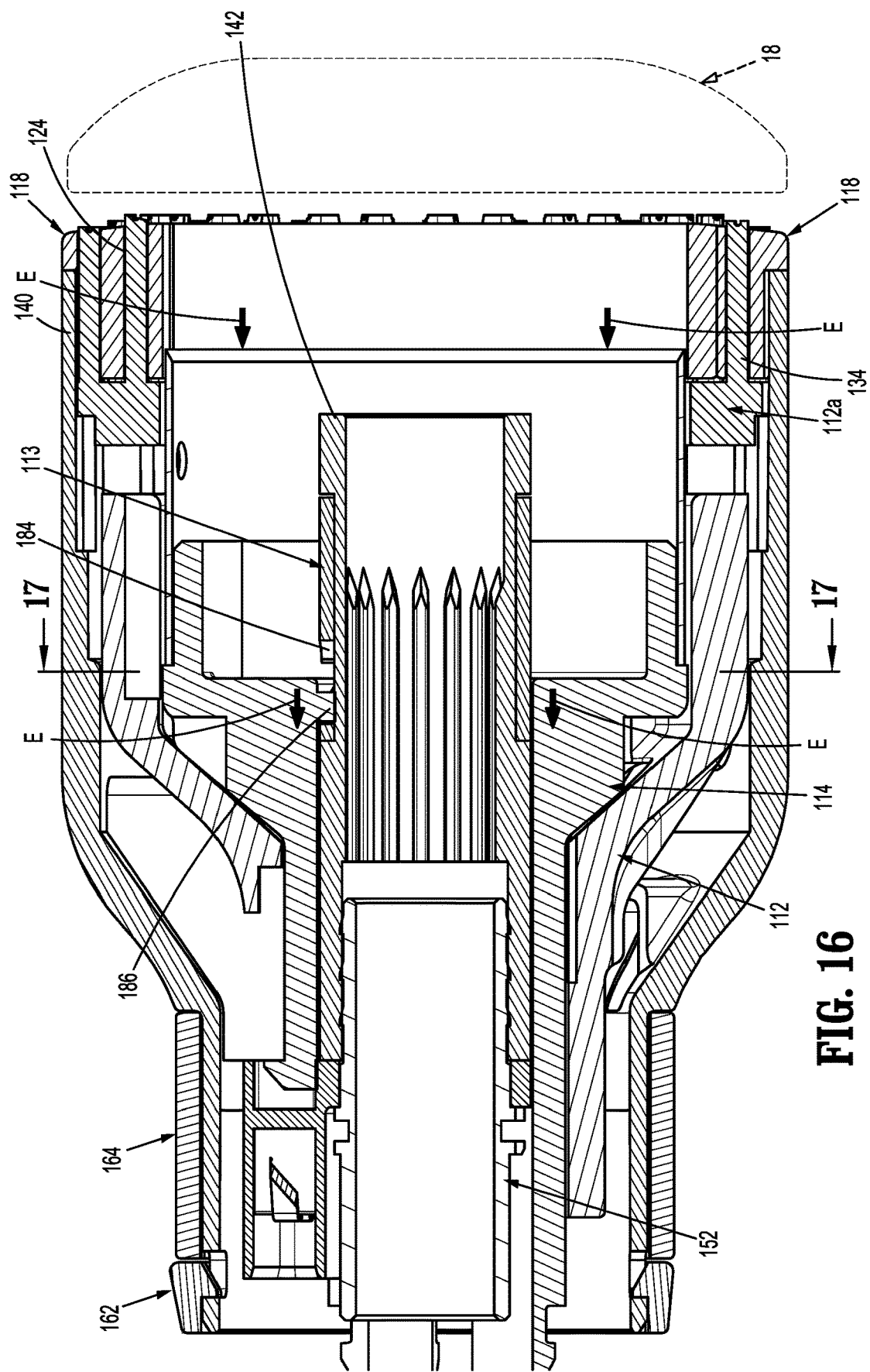
FIG. 16 is a cross-sectional view taken along section line 8-8 of FIG. 2 with the reload assembly in a fired position and the knife carrier in a retracted position.

Referring to FIGS. 16-19, when the knife carrier 114 is retracted about the inner housing portion 142 of the shell housing 110 in the direction indicated by arrows "E" in FIG. 16, the locking member 186 translates within the locking groove 184 in the direction indicated by arrows "F" from a distal end (FIG. 15) of the locking groove 184 to a proximal end (FIG. 19) of the locking groove 184. The locking groove 184 includes a second transverse portion 198 that communicates with a proximal end of the second axial portion 194 of the locking groove 184 and is defined by a second cam surface 200. The second transverse portion 198 of the locking groove 184 defines an acute angle with the longitudinal axis "X" of the reload assembly 100. As the locking member 184 translates through the locking groove 184 in the direction indicated by arrows "F", the locking member 186 engages the second cam surface 200 and rotates the locking collar 113 in the direction indicated by arrows "G" in FIG. 19 about the inner housing portion 142 of the shell housing 110. When the knife carrier 114 is in a post-fired retracted position, the locking member 186 is axially aligned with a locking portion 202 of the locking groove 184.

Referring to FIG. 20, if an attempt is made to advance the knife carrier 114 back to its advanced position after the reload 100 has been fired, the locking member 186 moves into the locking portion 202 of the locking groove 186 and engages a locking surface 204 formed at a distal end of the locking groove 184. The locking surface 204 obstructs readvancement of the knife carrier 114 and the knife 116 to safely retain the knife 116 within the shell housing 110 of the reload assembly 100. This minimizes a risk of injury to a clinician during manipulation and disposal of the reload assembly 100.

FIGS. 21-24 illustrate an alternative embodiment of the presently disclosed reload assembly in which the staple actuator 112' and the knife carrier 114' are modified to include the locking groove 184' and the locking member 186', respectively. Other aspects of the reload assembly including the staple actuator 112' and knife carrier 114' are as described above in regard to the staple actuator 112 and the knife carrier 114 and will not be described in further detail herein.

Figure 21:
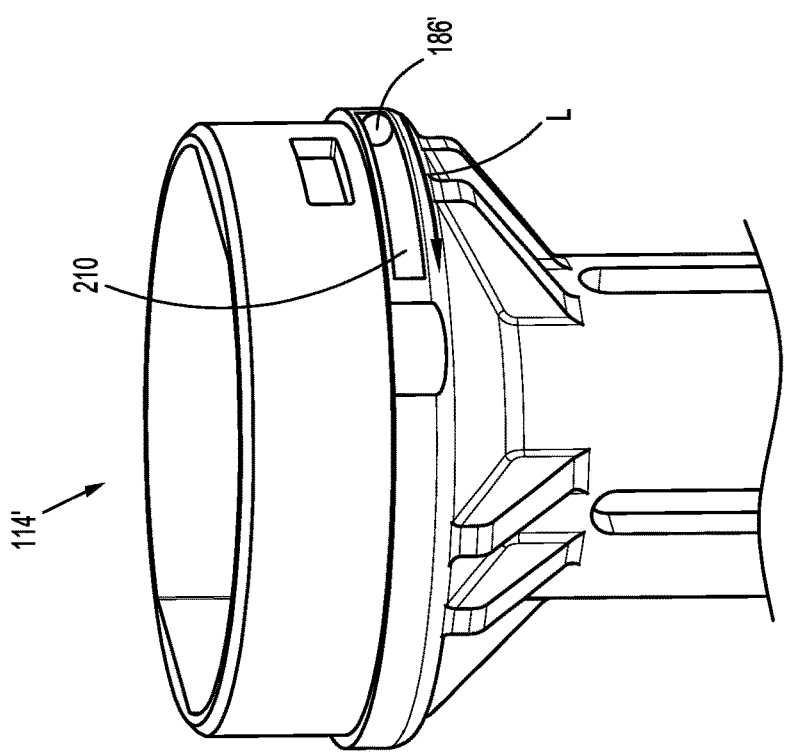
FIG. 21 is side perspective view of an alternate embodiment of the knife carrier of reload assembly shown in FIG. 2.

Referring to FIG. 21, the knife carrier 114' includes a channel 210 formed in an outer surface along a portion of the circumference of the knife carrier 114'. The channel 210 receives the locking member 186' and is dimensioned to allow movement of the locking member 186' from one end of the channel 210 to the other end of the channel 210. In embodiments, the locking member 186' includes a ball or other protrusion that can slide or roll within the channel 210.

Figure 22:
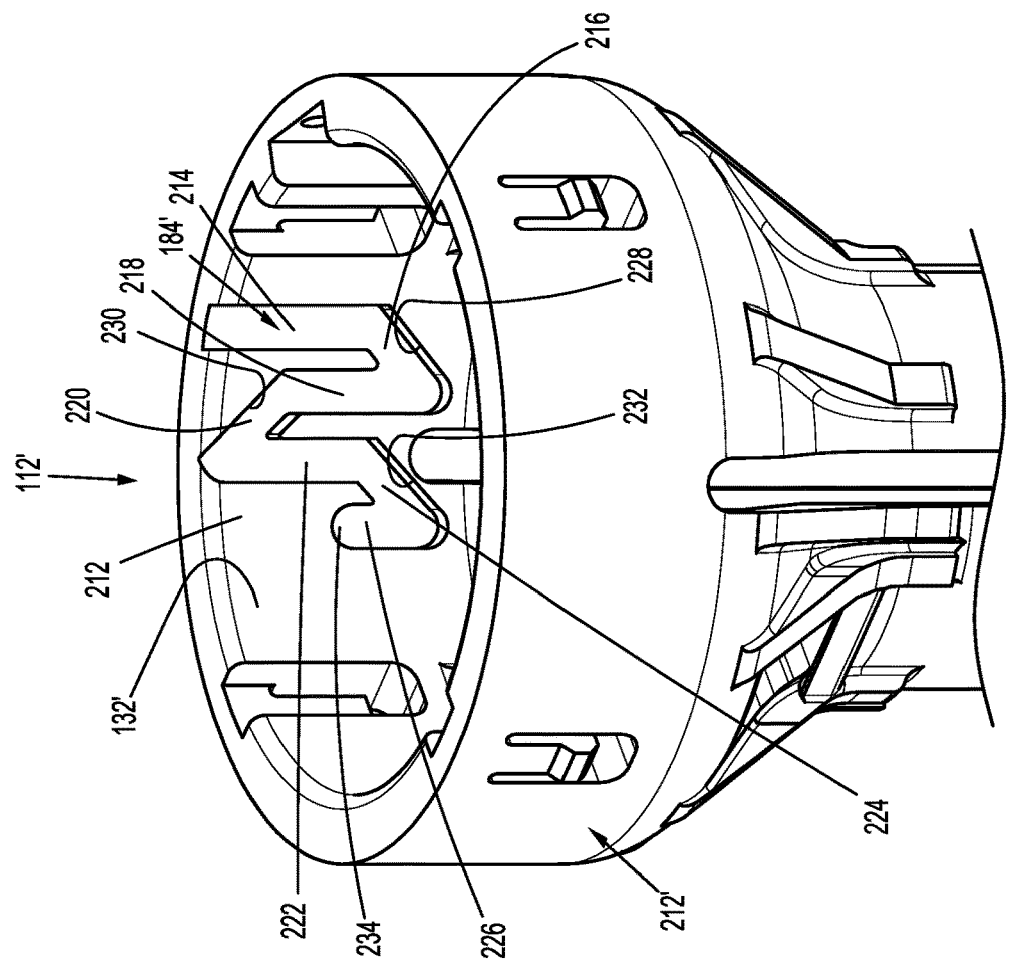
FIG. 22 is side perspective view of an alternate embodiment of the staple actuator of the reload assembly shown in FIG. 2.

Referring to FIG. 22, the staple actuator 112' defines a through bore 132' that receives the knife carrier 112'. The through bore 132' includes an inner wall 212 that defines the locking groove 184'. The locking groove 184' includes a first axial portion 214, a first transverse portion 216, a second axial portion 218, a second transverse portion 220, a third axial portion 222, a third transverse portion 224, and a locking portion 226. The first transverse portion 216 is defined in part by a first cam surface 228, the second transverse portion 220 is defined in part by a second cam surface 230, and the third transverse portion 224 is defined in part by a third cam surface 232. The end of the locking portion 226 of the locking groove defines a stop surface 234.

Figure 24:
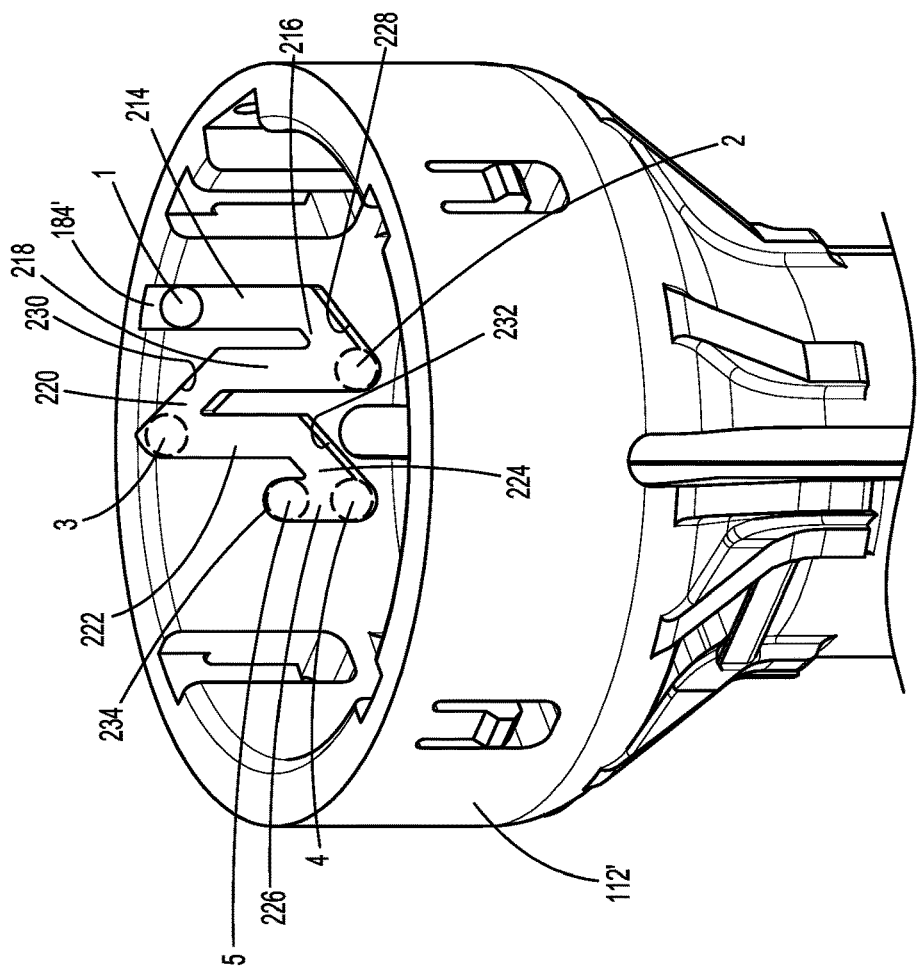
FIG. 24 is a perspective view from the distal end of the staple actuator showing a guide member of the knife carrier.
Figure 23:
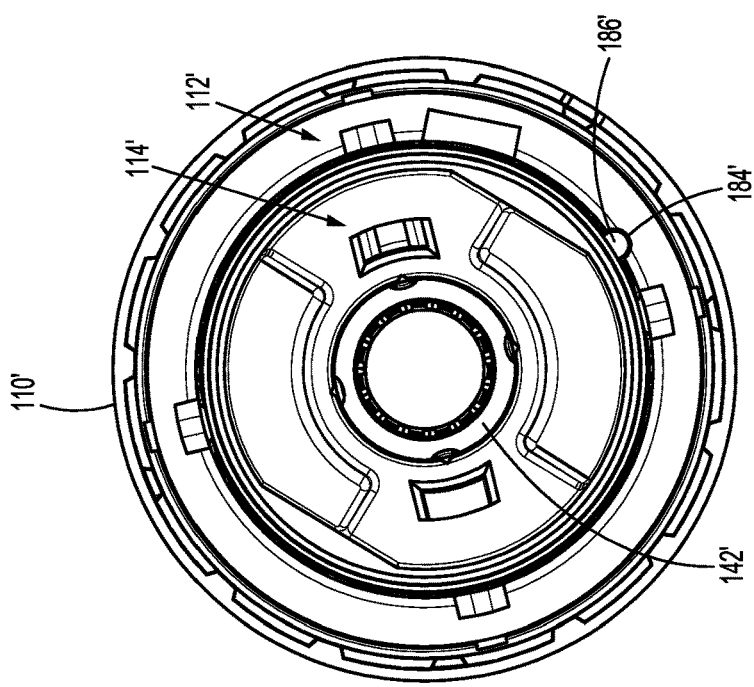
FIG. 23 is a view from the distal end of the knife carrier and staple actuator shown in FIGS. 21 and 22 assembled.
Figure 26:
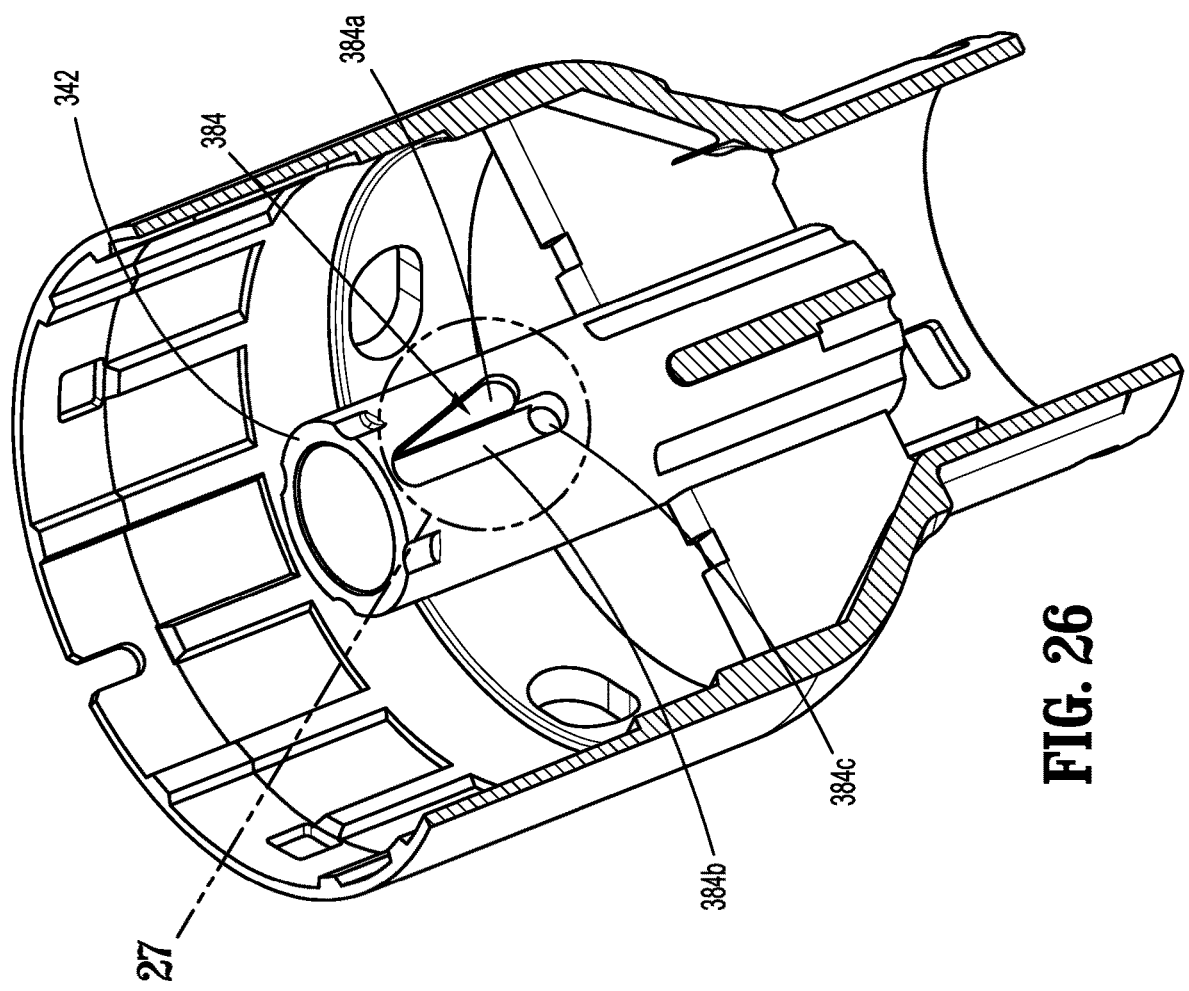
FIG. 26 is a side perspective, cross-sectional view of the shell housing of the reload assembly shown in FIG. 30.

Referring to FIGS. 23 and 24, when the reload assembly 100 including the modified staple actuator 112' and the knife carrier 114' is fired, the staple actuator 112' is moved within the shell housing 110' (FIG. 23) from its retracted position to its advanced position to eject staples 120 (FIG. 3) from the staple cartridge 118 independently of the knife carrier 114' as described above. When this occurs, the staple actuator 112' (FIG. 22) moves in relation to the knife carrier 114' and the locking member 186' (which are stationary) to move the locking member 186' through the first axial portion 214 and first transverse portion 216 of the locking groove 184' from position 1 (FIG. 22) towards position 2 (FIG. 24). When the locking member 186' engages the first cam surface 228 as it moves between position 1 and position 2, the locking member 186' is cammed or moved in the direction of arrow "L" (FIG. 21) within the channel 210.

After the staple actuator 112' is in its advanced position and the staples 120 have been fired, the knife carrier 114' is advanced from its retracted position to its advanced position to advance the knife 116 (FIG. 3) within the shell housing 110. As the knife carrier 114' moves from its retracted position towards its advanced position, the locking member 186' translates through the second axial portion 218 and the second transverse portion 220 of the locking groove 184' from position 2 (FIG. 24) to position 3. As the locking member 186' moves from position 2 to position 3, the locking member 186' engages the second cam surface 230 of the locking groove 184' defined in the staple actuator 112' and is moved further in the direction of arrow "L" within the channel 210 of the knife carrier 114'.

After the stapling device 10 (FIG. 1) is fired and the staple actuator 112' and the knife carrier 114' are in their advanced positions, the knife carrier 114' is moved from its advanced position back to its retracted position to withdraw the knife 116 (FIG. 3) back into the shell housing 110' (FIG. 23). As the knife carrier 114' is moves back to its retracted position, the locking member 186' moves within the third axial portion 222 and third transverse portion 224 of the locking groove 184' from position 3 to position 4. As the locking member 186' moves from position 3 to position 4, the locking member 186' engages the third cam surface 232 and is moved further in the direction of arrow "L" (FIG. 21) within the channel 210 of the knife carrier 114'. In position 4, the locking member 186' is positioned within the locking portion 226 of the locking groove 184' and is in alignment with the stop surface 234.

When the locking member 186' is aligned with the stop surface 234 of the locking portion 226 of the locking groove 184' and the knife 116 (FIG. 3) and knife carrier 114' are moved back towards their advanced positions, the locking surface 234 engages the locking member 186' (which is supported on the knife carrier 114') to obstruct readvancement of the knife carrier 114' and the knife 116 (FIG. 3) and safely retain the knife 116 within the shell housing 110' of the reload assembly 100. This minimizes risk of injury to a clinician during manipulation and disposal of the reload assembly 100.

Figure 30:
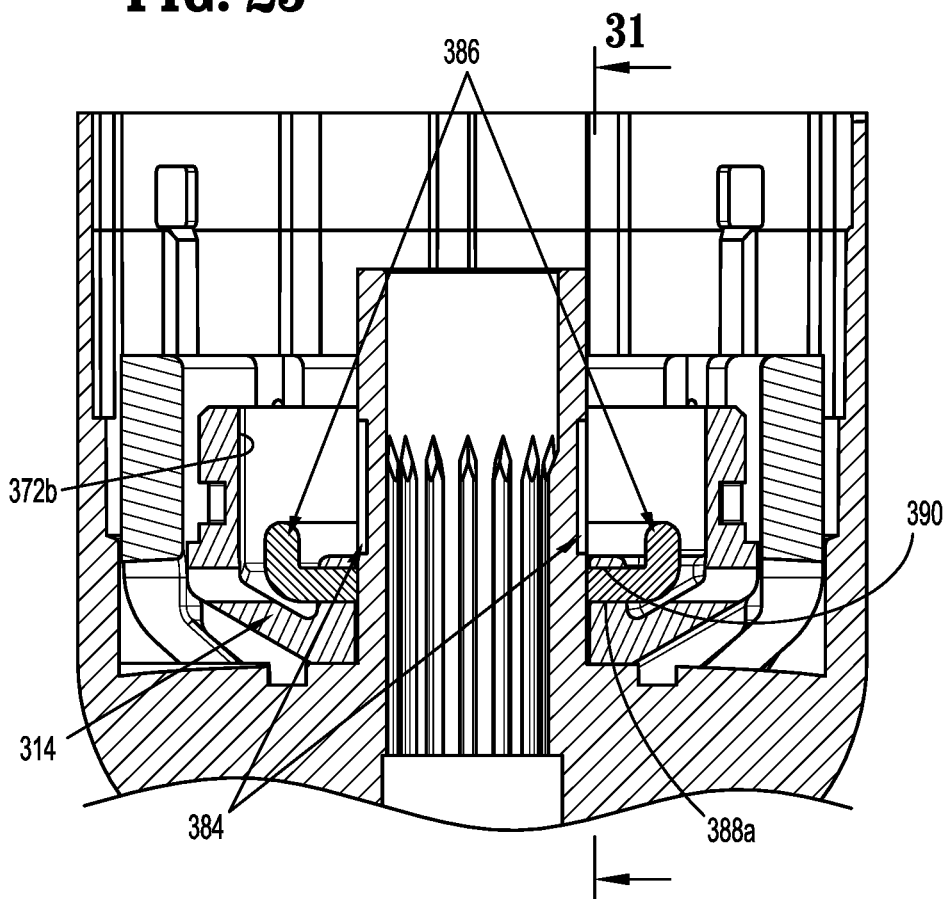
FIG. 30 is a cross-sectional view taken along section line 30-30 of FIG. 28.

FIGS. 25-31 illustrate another exemplary embodiment of the presently disclosed reload assembly shown generally as reload assembly 300 (FIG. 30). The reload assembly 300 is similar to the reload assemblies described above but the shell housing 310 and knife carrier 314 are modified to include or support the locking groove 384 and the locking member 386, respectively. The common features of the reload assembly 100 and reload 300 will not be described in further detail herein.

Figure 25:
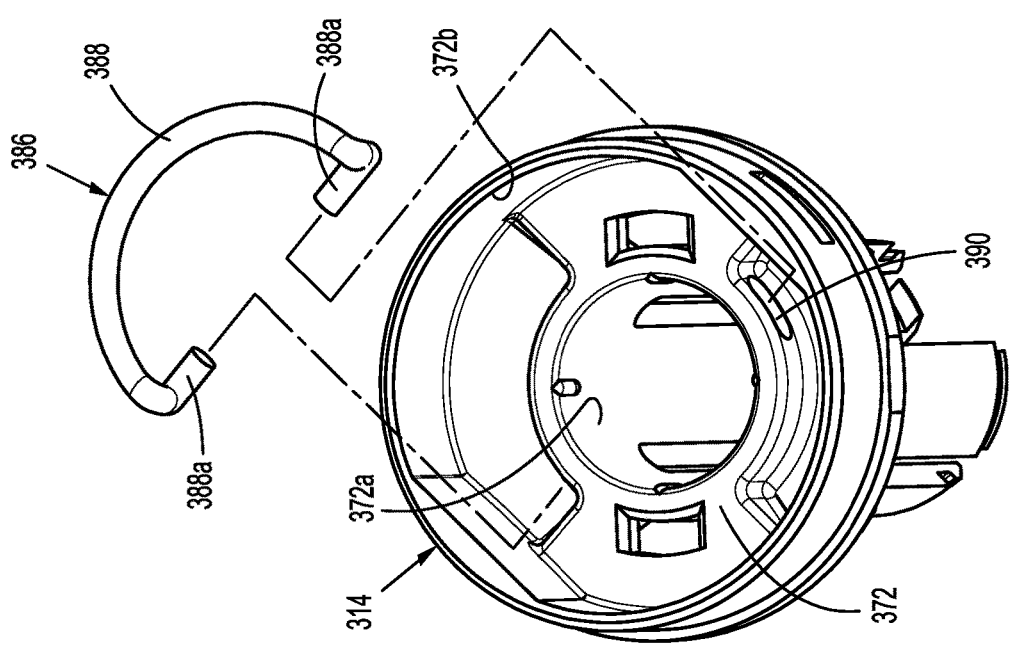
FIG. 25 is a perspective view of a locking member and knife carrier of another exemplary embodiment of the presently disclosed reload assembly shown in FIG. 30.
Figure 28:
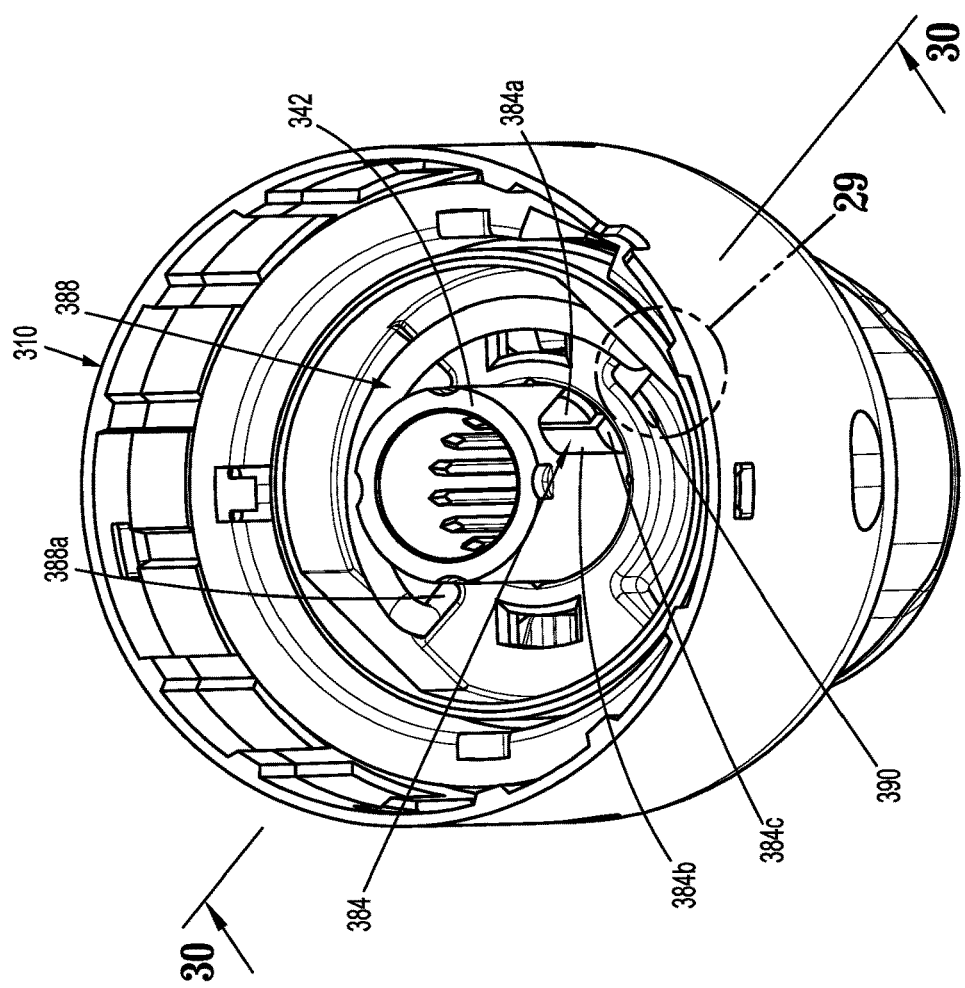
FIG. 28 is a perspective view from the distal end of the reload assembly shown in FIG. 30 with the staple cartridge removed and the knife carrier in a retracted position prior to firing of the reload assembly.
Figure 27:
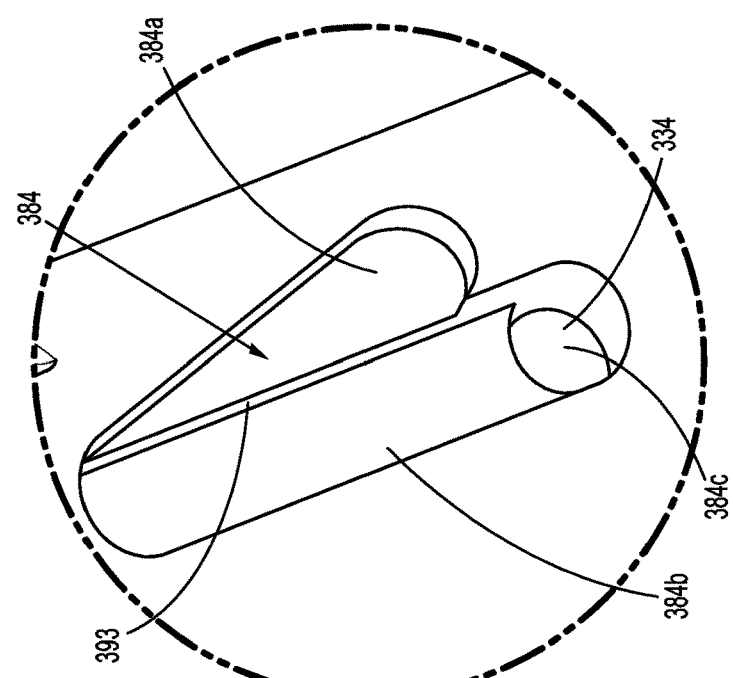
FIG. 27 is an enlarged view of the indicated area of detail shown in FIG. 26.
Figure 29:
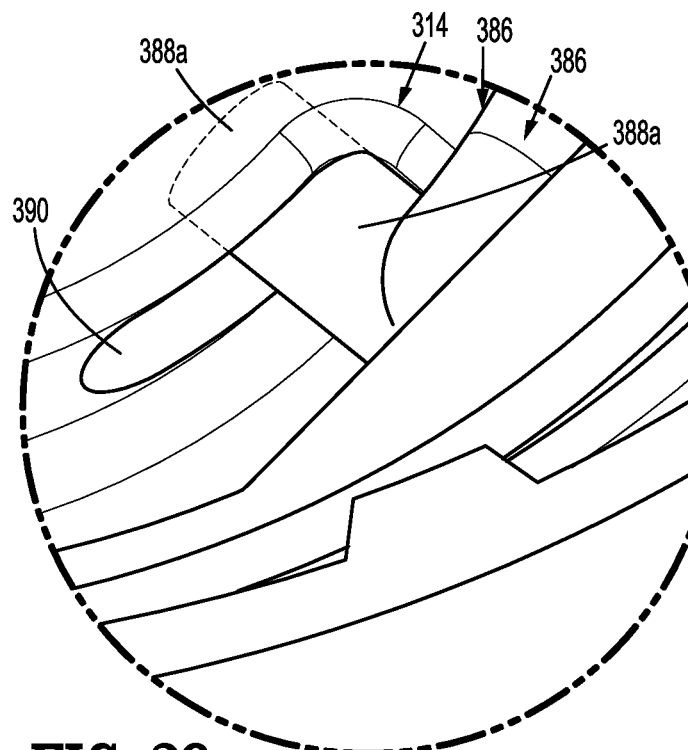
FIG. 29 is an enlarged view of the indicated area of detail shown in FIG. 28.

Referring to FIG. 25, the locking member 386 includes a resilient C-shaped body 388 that has spaced ends and is positioned within the larger diameter distal portion 372b (FIG. 25) of the central bore 372 of the knife carrier 314. Each of the spaced ends of the body 388 includes a transverse locking portion 388a that extends through an elongated opening 390 (FIG. 29) formed in the knife carrier 314. The elongated openings 390 are diametrically opposed to each other and communicate with the smaller diameter proximal portion 372a of the central bore 372 of the knife carrier 314 such that the transverse locking portions 388a extend into the smaller diameter portion 372a of the central bore 372 of the knife carrier 314.

Referring also to FIGS. 26-30, the inner housing portion 342 of the shell housing defines a locking groove 384. In embodiments, the locking groove 384 includes a first linear portion 384a and a second linear portion 384b. The first and second linear portions 384a, 384b distal portions that intersects with each other to define an acute angle. A proximal portion of the second linear portion 384b defines a locking bore 384c that includes an inner wall defining a stop surface 334. The first portion 384a of the locking groove 384 defines extends into the inner housing portion 342 of the shell housing 310 a first depth. Similarly, the second portion 384b of the locking groove 384 extends into the inner housing portion 342 of the shell housing 310 a second depth, and the locking bore 384c of the locking groove 384 extends into the inner housing portion 342 of the shell housing 310 a third depth. In embodiments, the second depth is greater than the first depth and the third depth is greater than the second depth. The depth of the first and second portions of the locking groove 384 and the locking bore 384c allows the transverse locking portions 388a of the locking member 386 to move from the first portion 384a of the locking groove 384, into the second portion 384b of the locking groove 384, and into the locking bore 384c but not in the reverse direction. In embodiments, the inner housing portion 342 of the shell housing 310 may include two diametrically opposed locking grooves 384 with each of the locking grooves 384 positioned to receive one of the transverse locking portions 388a of the locking member 386. Alternately, the inner housing portion 342 of the shell housing 310 need only define a single locking groove 384 and the locking member 386 need only include a single transverse locking portion 388a.

Figure 31:
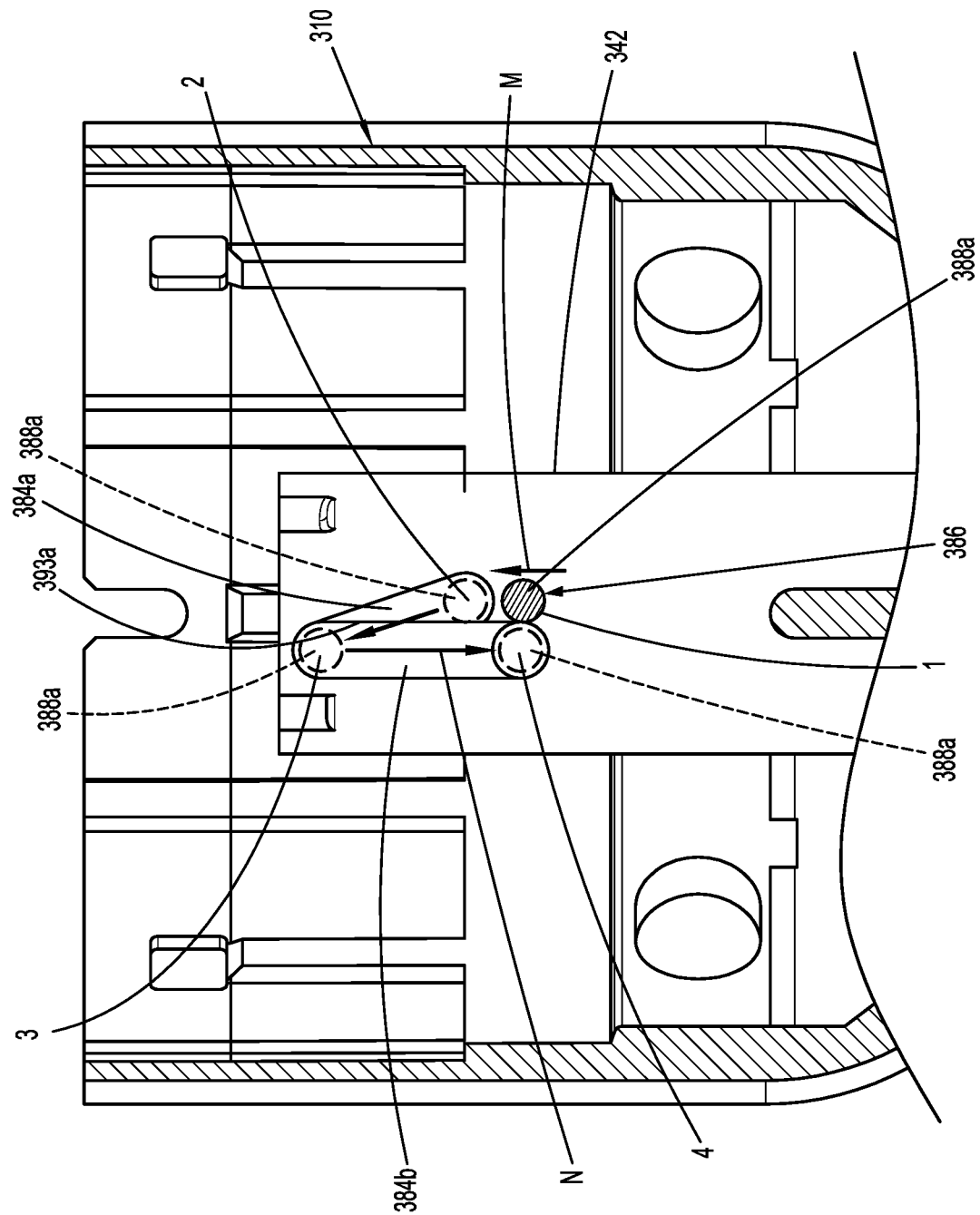
FIG. 31 is a cross-sectional view of the reload assembly shown in FIG. 30 with the staple cartridge removed showing the position of the locking member within a locking groove of the shell housing in the pre-fired retracted position, the advanced position, and the post-=fired retracted position of the knife carrier.

Referring also to FIG. 31, when the knife carrier 314 is positioned in its retracted position, the transverse locking portions 388a of the locking member 386 are positioned adjacent a proximal end of the first portion 384a of the locking groove 384 defined in the inner housing portion 342 of the shell housing 310. The transverse locking portions 388a are biased outwardly in tension via engagement with the inner housing portion 342 of the shell housing 310. With the transverse locking portions 388a of the locking member 386 in these positions, the knife carrier 314 is free to be advanced about the inner housing portion 342 within the shell housing 342.

After the reload assembly 310 is fired to eject staples as described above in regard to reload assembly 100, the knife carrier 314 is advanced in the direction indicated by arrow "M" (FIG. 31) from its retracted position to its advanced position to move the annular knife 116 (FIG. 3) to its advanced position. When the knife carrier 314 is moved towards its advanced position, the transverse locking portions 388a of the locking member 386 move into the first portion 384a of the locking grooves 384 and move through the locking grooves 384 to position 2 (FIG. 31). As the knife carrier 314 continues to move towards its advanced position, the transverse locking portions 388a of the locking member 386 move from the first portion 384a of the locking groove 384 and into the second portion 384b of the locking groove 384 to position 3 (FIG. 31). As discussed above, the depth of the second portion 384b of the locking groove 384 is greater than the depth of the first portion 384a of the locking groove 384 to define a shoulder 393a between the first and second portions of the locking groove 384. The shoulder 393a prevents movement of the transverse locking portions 388a back into the first portion 384a of the locking groove 384. The elongated openings 390 formed in the knife carrier 314 allow the transverse locking portions 388a to move laterally between the first and second portions of the locking groove 384.

When the knife carrier 314 is moved from its advanced position back towards its retracted position, the transverse locking portions 388a of the locking member 386 move within the second portion 384b of the locking groove 384 in the direction indicated by arrow "N" (FIG. 31) to a position in which the transverse locking portions 388a are aligned with the locking bore 384c. When the transverse locking portions 388a are aligned with the locking bore 384c, the transverse locking portions 388a, which are in tension, move or snap into the locking bore 384c due to the resilience of the locking member 384. Receipt of the locking portions 388a of the locking member 386 within the locking bores 384c lock the knife carrier 314 in its retracted position. As described above in regard to the previously described embodiments of the reload assembly, this structure minimizes the risk of injury to a clinician during manipulation and disposal of the reload assembly 100.

FIGS. 32-38 illustrate a shell housing 410 and knife carrier 414 of another exemplary embodiment of the presently disclosed reload assembly. In the presently disclosed embodiment, the shell housing 410 and knife carrier 414 are modified to include the locking member 486 and the locking groove 484, respectively. The common features of the reload assembly 100 and reload 300 will not be described in further detail herein.

Figure 32:
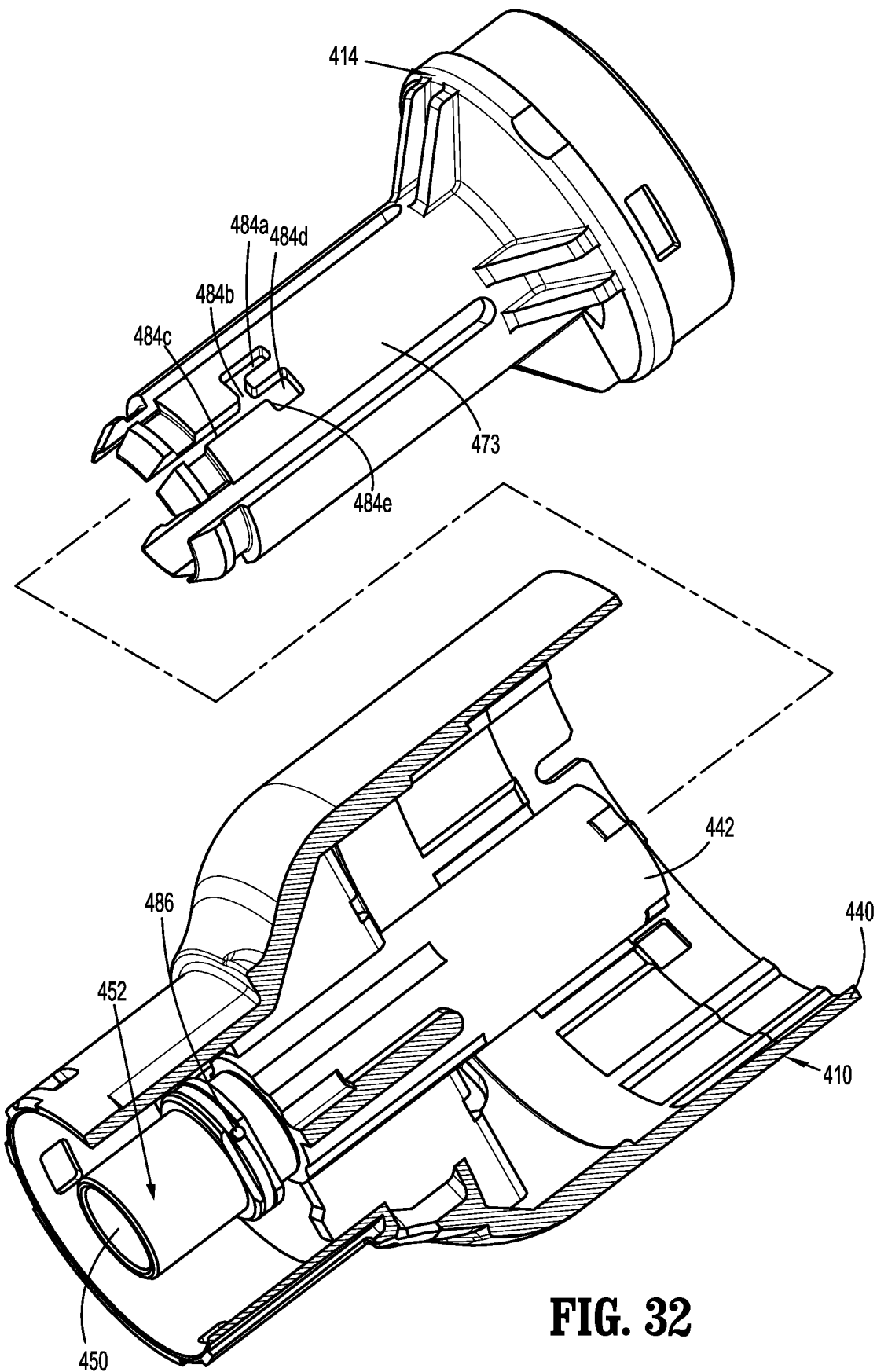
FIG. 32 is a an exploded perspective, partial cross-sectional view of another exemplary embodiment of the presently disclosed reload assembly with the staple cartridge removed.
Figure 33:
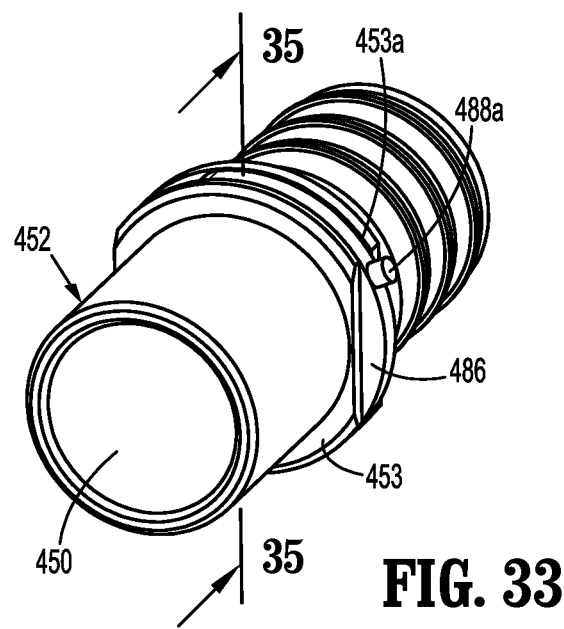
FIG. 33 is a perspective view from the proximal end of a bushing and snap ring assembly of the reload assembly shown in FIG. 32.
Figure 34:
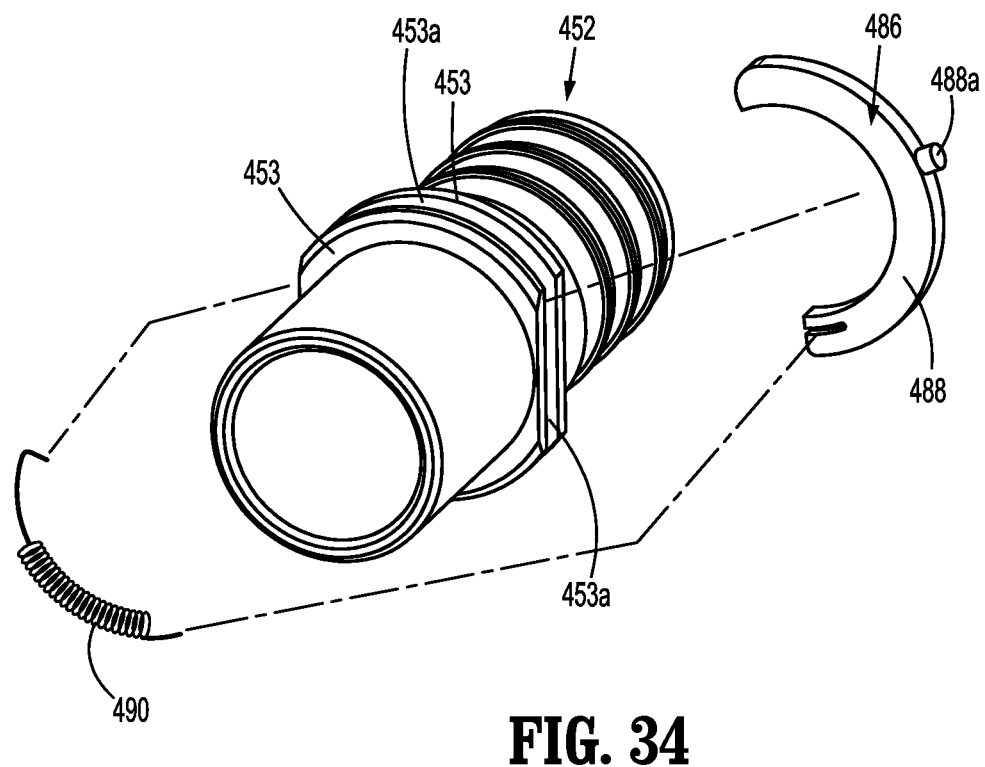
FIG. 34 is an exploded perspective view from the proximal end of the bushing and snap ring assembly of FIG. 33.

Referring to FIG. 32, the knife carrier 414 is substantially as described above except that the locking groove 484 is defined in one or more of the longitudinally extending body portions 473 of the knife carrier 414. In embodiments, the locking groove 484 extends through the body portion 473 of the knife carrier 414 and communicates with the central bore 474 of the knife carrier 414. The locking groove 484 includes a first linear portion 484a, a transverse portion 484b, a second linear portion 484c, and a lockout portion 484d defining a stop surface 484e.

As described above in regard to shell housing 110 (FIG. 3), the shell housing 410 includes an outer housing portion 440 and an inner housing portion 442. The inner housing portion 442 is received within the central bore 474 of the knife carrier 414 and defines a central bore (not shown). The knife carrier 414 moves in relation to the shell housing 410 between retracted and advanced positions to advance a knife 116 (FIG. 1) from a position confined within the shell housing 410 to a position extending from the shell housing 410. The proximal end of the inner housing portion 442 of the shell housing 410 receives a bushing 452 that defines a bore 450 that is coaxial to the bore (not shown) defined by the inner housing portion 442 of the shell housing 410.

Referring also to FIGS. 32-36, the bushing 452 includes a pair of spaced flanges 453 that define an annular recess 453a that receives the locking member 486. In embodiments, the locking member 486 includes a body 488 having a semi-circular configuration that is received within the recess 453a. The body 488 supports a transverse protrusion 488a that is received within a locking groove 484 of the knife carrier 414 as described below. In some embodiments, the locking member 486 is urged by a biasing member 490 to a position in which the transverse protrusion 488a is aligned with the stop surface 484e of the locking groove 484 as described below. The biasing member 490 can include a first end secured to the bushing 452 and a second end secured to the body 488 of the locking member 486 to urge the locking member 486 in the direction of arrow "P" in FIG. 35. Alternately, other biasing member configurations are envisioned.

Referring to FIGS. 36-38, when the knife carrier 414 is in its retracted position, the transverse protrusion 488a of the locking member 486 is positioned in a distal end of the first linear portion 484a of the locking groove 484 in the knife carrier 414. The biasing member 490 urges the transverse protrusion 488a in the direction "Q" as shown in FIG. 36.

When the knife carrier 414 is advanced about the inner housing portion 442 of the shell housing 410 in relation to the bushing 452 in the direction indicted by arrows "O" in FIG. 37, the transverse protrusion 488a of the locking member 486 moves from the distal end of the first linear portion 484a of the locking groove 484, through the transverse portion 484b of the locking groove 484, and through the second linear portion 484c of the locking groove 484 (FIG. 37). As discussed above, the biasing member 490 urges the transverse protrusion 488a in the direction "Q" (FIG. 36) so that transverse protrusion 488a translates through the locking groove 484 as the knife carrier 414 moves from its retracted position to its advanced position.

When the knife carrier 414 is returned to its retracted position in the direction indicated by arrows "R" in FIG. 38 after cutting of tissue is complete, the biasing member 490 urges the transverse protrusion 488a along the second linear portion 484c and into the lockout portion 484d in the direction indicated by arrow "R" in FIG. 38 to a position aligned with the stop surface 484e. In this position, the transverse protrusion 488a obstructs movement of the knife carrier 414 towards its advanced position to minimize the risk of injury to a clinician during manipulation and disposal of the reload assembly 100.

FIGS. 39-44 illustrate a knife carrier 514 and a shell housing 510 of another exemplary embodiment of the presently disclosed reload assembly in which slight modifications have been made to the shape of the locking groove 584 to obviate the need for a biasing member. Applicant notes that the shell housing 510, bushing 552, and locking member 586 are as described above in regard to shell housing 410, bushing 452, and the locking member 486 and will not be described in further detail herein.

Referring to FIG. 39, the locking groove 584 includes a first linear portion 584a, a first angled portion 584b, a second linear portion 584c, a second angled portion 584d and a locking portion 584e. The locking portion 584d includes a stop surface 584f. Each of the first and second angled portions 584b and 584d include cam surfaces or guide walls 585 that direct the transverse protrusion 588a through the locking groove 584 towards the locking portion 584 and into axial alignment with the stop surface 584f.

Figure 41:
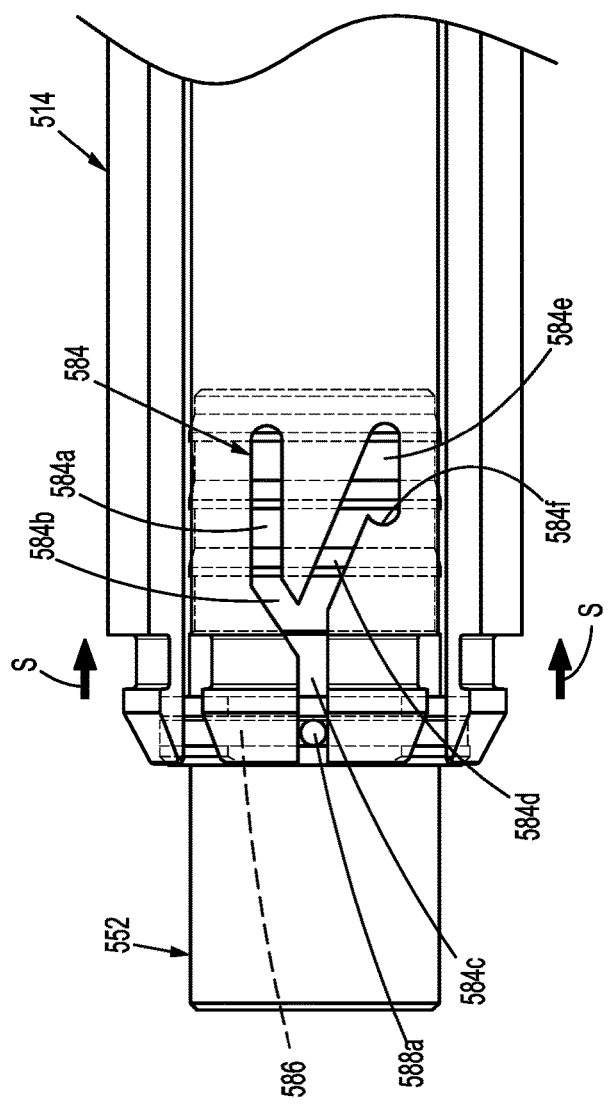
FIG. 41 is a side perspective view of the knife carrier of the reload assembly and the bushing and snap ring assembly shown in FIG. 40 with the bushing and snap ring assembly shown partially in phantom and the knife carrier in its advanced position.

Referring to FIGS. 40 and 41, when the knife carrier 514 is advanced from its retracted position (FIG. 39) towards its advanced position (FIG. 40) in the direction indicated by arrows "S", the transverse protrusion 588a of the locking member 586 moves from the distal end of the first linear portion 584a of the locking groove 584, through the first angled portion 584b of the locking groove 584, to a proximal end of the second linear portion 584c of the locking groove 584. As the transverse protrusion 588a passes through the first angled portion 584b of the locking groove 584, the cam surface 585 guides the transverse protrusion 588a into the second linear portion 584c of the locking groove 584.

Figure 42:
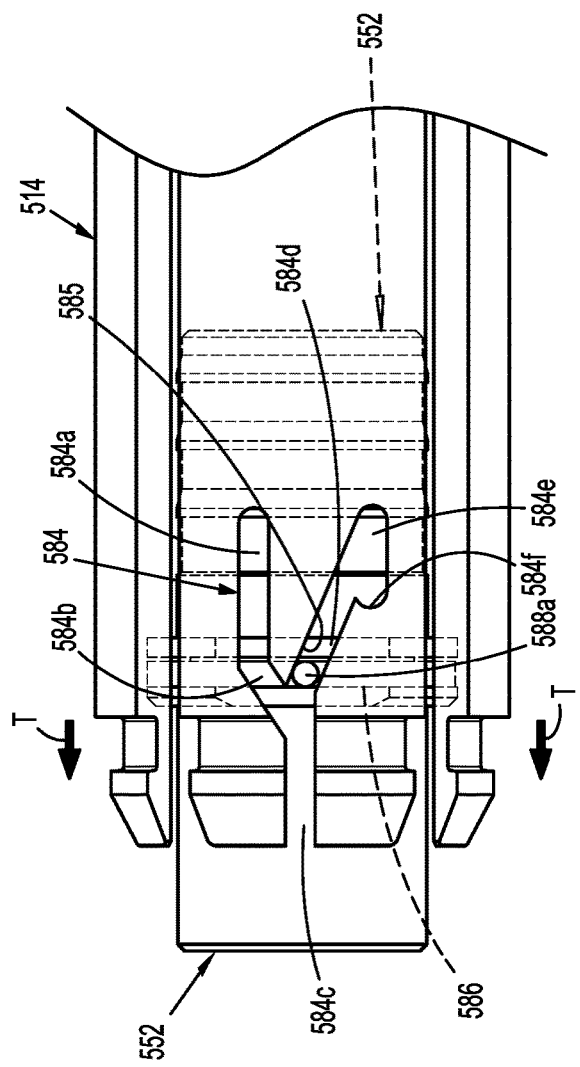
FIG. 42 is a side perspective view of the knife carrier of the reload assembly and the bushing and snap ring assembly shown in FIG. 41 with the bushing and snap ring assembly shown partially in phantom and the knife carrier moving back towards its retracted position.

Referring to FIGS. 42 and 43, when the knife carrier 514 is returned to its retracted position (FIG. 43) in the direction indicated by arrows "T" in FIG. 42, the transverse protrusion 588a translates through the second linear portion 584c of the locking groove 584 and the second angled portion 584d of the locking groove 584 and passes into the locking portion 584e of the locking groove 584 to a position aligned with the stop surface 584f. As the transverse protrusion 588a passes from the second linear portion 584c of the locking groove 584 into the second angle portion 584d, the cam surface 585 defining the second angled portion 584d guides and directs the transverse protrusion 588a into the locking portion 584e to a position axially aligned with the stop surface 584f.

Referring to FIG. 44, when the transverse protrusion 588a is axially aligned with the stop surface 584f, any attempt to move the knife carrier 514 towards its advanced position in the direction indicated by arrows "U" in FIG. 44 moves the transverse protrusion 588a into engagement with the stop surface 584f to obstruct movement of the knife carrier 514 and knife 116 (FIG. 3) towards its advanced position the reload assembly has been fired. This retains the knife within the shell housing 110 (FIG. 3) to minimize the risk of injury to a clinician during manipulation and disposal of the reload assembly 100.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A reload assembly comprising:
   a shell housing including an inner housing portion and an outer housing portion, the inner housing portion spaced from the outer housing portion to define an annular cavity between the inner and outer housing portions;

a staple cartridge supported on a distal portion of the shell housing, the staple cartridge having a plurality of staple pockets, each of the staple pockets receiving a staple;

a staple actuator supported within the annular cavity, the staple actuator movable between a retracted position and an advanced position when the reload assembly is fired to eject the staples from the staple cartridge;

a knife carrier including a body defining a longitudinal axis and supporting a knife, the body of the knife carrier including an inner wall defining a central bore, the inner housing portion of the shell housing being positioned within the central bore of the knife carrier such that the knife carrier is movable about the inner housing portion of the shell housing between advanced and retracted positions when the reload assembly is fired;

wherein one of the knife carrier or the shell housing defines a locking groove and the other of the knife carrier and the shell housing supports a locking member, the locking groove having a first end portion and a second end portion, the locking member being received within the first end portion of the locking groove and movable through the locking groove to the second end portion of the locking groove to prevent readvancement of the knife carrier after the reload assembly is fired.

2. The reload assembly of claim 1, wherein the second end portion of the locking groove defines a stop surface that is positioned to engage the locking member when the locking member is returned to its retracted position after the reload assembly is fired.

3. A reload assembly comprising:

a shell housing including an inner housing portion and an outer housing portion, the inner housing portion spaced from the outer housing portion to define an annular cavity between the inner and outer housing portions;

a staple cartridge supported on a distal portion of the shell housing, the staple cartridge having a plurality of staple pockets, each of the staple pockets receiving a staple;

a staple actuator supported within the annular cavity, the staple actuator movable between a retracted position and an advanced position to eject the staples from the staple cartridge;

a knife carrier including a body defining a longitudinal axis and supporting a knife, the body of the knife carrier including an inner wall defining a central bore, the inner housing portion of the shell housing being positioned within the central bore of the knife carrier such that the knife carrier is movable about the inner housing portion of the shell housing between advanced and retracted positions;

wherein one of the knife carrier or the shell housing defines a locking groove and the other of the knife carrier and the shell housing supports a locking member, the locking groove having a first end and a second end, the locking member being received within and movable through the locking groove, the second end of the locking groove defining a stop surface that is positioned to engage the locking member when the locking member is returned to its retracted position to prevent readvancement of the knife carrier after the reload assembly is fired; and a locking collar supported on the inner housing portion, the locking groove being defined by the locking collar.

4. The reload assembly of claim 3, wherein the locking member includes a protrusion supported on the knife carrier, the protrusion being received within the locking groove of the locking collar.

5. The reload assembly of claim 4, wherein the locking collar is rotatably supported on the inner housing portion of the shell housing, the locking collar being rotatable from an unlocked position to a locked position in response to movement of the knife carrier between its advanced and retracted positions.

6. The reload assembly of claim 3, wherein the locking collar is axially fixed about the inner housing portion of the shell housing.

7. The reload assembly of claim 1, wherein the locking groove is defined in the inner housing portion of the shell housing and the locking member is supported on the knife carrier.

8. The reload assembly of claim 7, wherein the locking member includes a resilient C-shaped body having spaced ends, the C-shaped body supported on the knife carrier such that at least one of the spaced ends is positioned within the central bore of the knife carrier and is received within the locking groove.

9. The reload assembly of claim 8, wherein the locking groove includes a first locking groove defined in one side of the inner housing portion of the shell housing and a second locking groove defined in an opposite side of the inner housing portion of the shell housing, each of the first and second locking grooves receiving one of the spaced ends of the C-shaped body.

10. The reload assembly of claim 8, wherein the locking groove includes a first linear portion, a second linear portion, and a stop surface positioned at one end of the second linear portion, the first linear portion intersecting the second linear portion.

11. The reload assembly of claim 10, wherein the stop surface is defined within a locking bore.

12. The reload assembly of claim 11, wherein the first linear portion has a first depth, the second linear portion has a second depth, and the locking bore has a third depth, the second depth being greater than the first depth and the third depth being greater than the second depth.

13. The reload assembly of claim 2, wherein the locking groove is defined in the knife carrier and the locking member is supported on the inner housing portion of the shell housing.

14. The reload assembly of claim 13, wherein the locking member is rotatably supported on the inner housing portion of the shell housing and includes a protrusion that is received within the locking groove, the locking member being rotatable from an unlocked position to a locked position in which the protrusion is aligned with the stop surface.

15. The reload assembly of claim 14, further including a biasing member positioned to urge the locking member towards the locked position.

16. The reload assembly of claim 14, wherein the locking groove includes a first linear portion, a first transverse portion, a second linear portion, a second transverse portion, and a lockout portion, the stop surface positioned within the lockout portion.

17. The reload assembly of claim 16, further including cam surfaces defining at least a portion of the first and second transverse portions of the locking groove, the cam surfaces engaging the protrusion of the locking member to move the locking member towards the locked position in response to movement of the knife carrier between the retracted and advanced positions.

18. A reload assembly comprising:
- a shell housing including an inner housing portion and an outer housing portion, the inner housing portion spaced from the outer housing portion to define an annular cavity between the inner and outer housing portions;
- a staple cartridge supported on a distal portion of the shell housing, the staple cartridge having a plurality of staple pockets, each of the staple pockets receiving a staple;
- a staple actuator supported within the annular cavity and defining a longitudinal through bore, the staple actuator movable between a retracted position and an advanced position when the reload assembly is fired to eject the staples from the staple cartridge;
- a knife carrier including a body defining a longitudinal axis and supporting a knife, the body of the knife carrier including an inner wall defining a central bore, the knife carrier movable about the inner housing portion of the shell housing within the staple actuator between advanced and retracted positions when the reload assembly is fired;
- wherein one of the knife carrier and the staple actuator defines a locking groove and the other of the knife carrier and the staple actuator supports a locking member, the locking groove having a first end portion and a second end portion, the locking member being received within the first end portion of the locking groove and movable through the locking groove to the second end of the locking groove to prevent readvancement of the knife carrier after the reload assembly is fired.

19. The reload assembly of claim 18, wherein the second end portion of the locking groove defines a stop surface that is positioned to engage the locking member when the locking member is returned to its retracted position after the reload assembly is fired to obstruct readvancement of the knife carrier.

20. The reload assembly of claim 19, wherein the locking member includes a protrusion supported within a channel defined in the knife carrier.

21. The reload assembly of claim 20, wherein the channel is elongated to allow for lateral movement of the protrusion within the channel in response to movement of the knife carrier between its advanced and retracted positions.

* * * * *